(12) United States Patent
Su et al.

(10) Patent No.: US 11,779,861 B2
(45) Date of Patent: *Oct. 10, 2023

(54) USE OF ELECTROCHEMICAL DEVICES OR SYSTEMS COMPRISING REDOX-FUNCTIONALIZED ELECTRODES FOR BIOSEPARATION AND BIOCATALYSIS

(71) Applicant: Massachusetts Institute of Technology, Cambridge, MA (US)

(72) Inventors: Xiao Su, Cambridge, MA (US); Trevor Alan Hatton, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1126 days.

This patent is subject to a terminal disclaimer.

(21) Appl. No.: 16/345,676

(22) PCT Filed: Oct. 27, 2017

(86) PCT No.: PCT/US2017/058888
§ 371 (c)(1),
(2) Date: Apr. 26, 2019

(87) PCT Pub. No.: WO2018/081653
PCT Pub. Date: May 3, 2018

(65) Prior Publication Data
US 2019/0240595 A1    Aug. 8, 2019

Related U.S. Application Data

(60) Provisional application No. 62/413,960, filed on Oct. 27, 2016.

(51) Int. Cl.
*B01D 15/38* (2006.01)
*C07K 1/24* (2006.01)
(Continued)

(52) U.S. Cl.
CPC ..... *B01D 15/3885* (2013.01); *B01D 15/3804* (2013.01); *C07K 1/24* (2013.01); *C07K 14/765* (2013.01); *C07K 14/805* (2013.01); *C12N 9/0065* (2013.01); *C12N 9/22* (2013.01); *C12N 9/2462* (2013.01); *C12N 9/6427* (2013.01);
(Continued)

(58) Field of Classification Search
CPC ...... C07K 1/24; C12N 15/10; G01N 27/3276; G01N 27/3277; B01D 15/388
See application file for complete search history.

(56) References Cited

U.S. PATENT DOCUMENTS 4,830,959 A * 5/1989 McNeil ............... G01N 33/581
435/817
5,776,351 A    7/1998 McGinness et al.
(Continued)

OTHER PUBLICATIONS

Tran et al., Langmuir 27(10): 6201-6210 (2011).*
(Continued)

*Primary Examiner* — Caitlyn Mingyun Sun
(74) *Attorney, Agent, or Firm* — Wolf, Greenfield & Sacks, P.C.

(57) ABSTRACT

Various aspects described herein relate to electrochemical devices, e.g., for separation of one or more biomolecules from a solution, and methods of using the same. Methods for using the electrochemical devices for biocatalysis are also described herein.

28 Claims, 14 Drawing Sheets

(51) Int. Cl.
  C12N 15/10    (2006.01)
  H01M 4/90     (2006.01)
  G01N 27/327   (2006.01)
  H01M 8/18     (2006.01)
  H01M 10/36    (2010.01)
  C07K 14/765   (2006.01)
  C07K 14/805   (2006.01)
  C12N 9/08     (2006.01)
  C12N 9/22     (2006.01)
  C12N 9/36     (2006.01)
  C12N 9/76     (2006.01)
  C12N 13/00    (2006.01)

(52) U.S. Cl.
  CPC ............ *C12N 13/00* (2013.01); *C12N 15/10* (2013.01); *C12N 15/1003* (2013.01); *C12Y 111/01007* (2013.01); *C12Y 301/27005* (2013.01); *C12Y 302/01017* (2013.01); *C12Y 304/21001* (2013.01); *G01N 27/3276* (2013.01); *G01N 27/3277* (2013.01); *H01M 4/90* (2013.01); *H01M 8/188* (2013.01); *H01M 10/36* (2013.01); *B01D 15/388* (2013.01); *H01M 4/9008* (2013.01); *H01M 4/9083* (2013.01); *Y02E 60/50* (2013.01)

(56) References Cited

U.S. PATENT DOCUMENTS

| | | | |
|---|---|---|---|
| 6,281,006 | B1 | 8/2001 | Heller et al. |
| 7,435,362 | B2* | 10/2008 | Muraoka ............... H10K 10/701 |
| | | | 430/270.16 |
| 8,436,116 | B2 | 5/2013 | Akhoury et al. |
| 8,506,779 | B2 | 8/2013 | Kahn et al. |
| 10,766,795 | B2* | 9/2020 | Su ........................ C02F 1/469 |
| 2002/0163135 | A1 | 11/2002 | Kato et al. |
| 2005/0227071 | A1 | 10/2005 | Muraoka et al. |
| 2009/0082653 | A1* | 3/2009 | Rohde ................ A61B 5/02042 |
| | | | 600/347 |
| 2009/0283424 | A1* | 11/2009 | Carson ................... B82Y 15/00 |
| | | | 205/792 |
| 2010/0222519 | A1 | 9/2010 | Akhoury et al. |
| 2011/0031440 | A1 | 2/2011 | Palmore et al. |
| 2012/0186999 | A1* | 7/2012 | Walton ................. G01N 33/497 |
| | | | 977/773 |
| 2012/0286653 | A1* | 11/2012 | Abe ......................... H10K 50/11 |
| | | | 313/504 |
| 2014/0166485 | A1* | 6/2014 | Sailor .................... G01N 27/447 |
| | | | 204/450 |
| 2014/0332406 | A1 | 11/2014 | Nottke et al. |
| 2014/0346046 | A1 | 11/2014 | Andelman |
| 2015/0322475 | A1* | 11/2015 | Cheng ..................... C12Q 1/004 |
| | | | 427/125 |
| 2016/0138174 | A1 | 5/2016 | Hatton et al. |
| 2017/0113951 | A1 | 4/2017 | Su et al. |
| 2018/0215635 | A1 | 8/2018 | Roberts et al. |
| 2020/0399146 | A1 | 12/2020 | Su et al. |

OTHER PUBLICATIONS

Isoelectric point—Wikipedia (Year: 2022).*
N.V. Bhagavan, Protein Isolation and Determination of Amino Acid Sequence, Medical Biochemistry (Fourth Edition), 2002, Chapter 3, p. 35-50. (Year: 2002).*
U.S. Appl. No. 15/336,637, filed Oct. 27, 2016, Su et al.
PCT/US2016/059193, Jan. 3, 2017, International Search Report and Written Opinion.
PCT/US2016/059193, May 11, 2018, International Preliminary Report on Patentability.
International Search Report and Written Opinion for Application No. PCT/US2016/059193 dated Jan. 3, 2017.
International Preliminary Report on Patentability for Application No. PCT/US2016/059193 dated May 11, 2018.
Achilleos et al. Selective molecularly mediated pseudocapacitive separation of ionic species in solution. ACS Appl Mater Interf. 2016;8(48):32743-53. Epub Oct. 4, 2016.
Akhoury et al., Redox-responsive gels with tunable hydrophobicity for controlled solubilization and release of organics. ACS Appl Mater Interf. 2011;3(4):1167-74. Epub Mar. 16, 2011.
Alsbaiee et al., Rapid removal of organic micropollutants from water by a porous β-cyclodextrin polymer. Nature. Jan. 14, 2016;529(7585):190-4. Suppl Info, 11 pages, doi: 10.1038/nature16185. Epub Dec. 21, 2015.
Angamuthu et al., Electrocatalytic CO2 conversion to oxalate by a copper complex. Science. Jan. 15, 2010;327(5963):313-5. doi: 10.1126/science.1177981.
Anzenbacher et al., Simple electrooptical sensors for inorganic anions. Org Lett. Oct. 27, 2005;7(22):5027-30. Epub Oct. 1, 2005.
Augustyn et al., Pseudocapacitive oxide materials for high-rate electrochemical energy storage. Energy Environ Sci. 2014;7(5):1597-1614. Accessed online at http://oatao.univ-toulous.fr/eprintsID:13900. 20 pages.
Aydin et al., Electrocatalytic conversion of $CO_2$ on a polypyrrole electrode under high pressure in methanol. Synth Met. Jul. 8, 2004;144(1):75-80.
Beer et al., Anion recognition and sensing: The state of the art and future perspectives. Angew Chem Int Ed Engl. Feb. 2, 2001;40(3):486-516.
Beer et al., Anion recognition and luminescent sensing by new ruthenium(II) and rhenium(I) bipyridyl calix[4]diquinone receptors. Chem Commun. 1999;0:1755-6. Comm 9/05277A.
Bernardo et al., Cyclobis(paraquat-p-phenylene) as a synthetic receptor for electron-rich aromatic compounds: Electrochemical and spectroscopic studies of neurotransmitter binding. J Am Chem Soc. Dec. 1992;114(26):10624-31.
Burkhardt et al., Tailored redox functionality of small organics for pseudocapacitive electrodes. Energy Environ Sci. 2012;5:7176-87. Epub Apr. 10, 2012.
Chen et al., Highly stable nickel hexacyanoferrate nanotubes for electrically switched ion exchange. Adv Funct Mater. Oct. 2007;17(15):2943-8. Epub Aug. 28, 2007.
Das et al., Ru(II) and Os(II) mixed-chelates derived from imidazole-4,5-dicarboxylic acid and 2,2'-bipyridine as colorimetric sensors for anions: Synthesis, characterization and binding studies. Dalton Trans. May 7, 2010;39(17):4162-9. doi: 10/1039/b924561h. Epub Mar. 24, 2010.
Dash et al., Electrochemical separation: Promises, opportunities, and challenges to develop next-generation radionuclide generators to meet clinical demands. Ind Eng Chem Res. 2014;53(10):3766-77. Epub Feb. 20, 2014.
Evans et al., Advances in anion supramolecular chemistry: From recognition to chemical applications. Angew Chem Int Ed. Oct. 27, 2014;53(44):11716-54.
Gallei et al., Recent advances in immobilized ferrocene-containing polymers. Ch 5 in Functional Metallosupramolecular Materials. Royal Society of Chemistry, Cambridge. Jul. 2015. pp. 120-148.
Ge et al., Ion exchange properties of polypyrrole. Reactive Polymers. Oct. 1992;18(2):133-140.
Grimm et al., Review of electro-assisted methods for water purification. Desalination. 1998;115:285-94.
Hull et al., Reversible hydrogen storage using $CO_2$ and a proton-switchable iridium catalyst in aqueous media under mild temperatures and pressures. Nat Chem. May 2012;4(5):383-8. doi: 10.1038/nchem.1295. Epub Mar. 18, 2012.
Kang et al., Rapid selective electrocatalytic reduction of carbon dioxide to formate by an iridium pincer catalyst immobilized on carbon nanotube electrodes. Angew Chem Int Ed Engl. Aug. 11, 2014;53(33):8709-13. doi: 10.1002/anie.201310722. Epub Jun. 4, 2014.
Khin et al., A review on nanomaterials for environmental remediation. Energy Environ Sci. 2012;5:8075-109. Epub May 24, 2012.

(56) References Cited

OTHER PUBLICATIONS

Kim et al., CDI ragone plot as a functional tool to evaluate desalination performance in capacitive deionization. RSC Adv. 2015;5:1456-61. Epub Nov. 27, 2014. Accepted author manuscript, 16 pgs.

Kushi et al., Remarkable decrease in overpotential of oxalate formation in electrochemical $CO_2$ reduction by a metal-sulfide cluster. J Chem Soc, Chem Commun. 1995;0:1223-4. Epub Jan. 1, 1995.

La Mantia et al., Batteries for efficient energy extraction from a water salinity difference. Nano Lett. Apr. 13, 2011;11(4):1810-3. doi: 10.1021/nl200500s. Epub Mar. 17, 2011.

MacFarland et al., Rotor-shaped cyclopentadienyltetraphenylcyclobutadienecobalt. An advanced inorganic experiment. J Chem Educ. Jan. 2005;82(1);109-10. Epub Jan. 1, 2005.

Mao et al., Metallocene/carbon hybrids prepared by a solution process for supercapacitor applications. J Mater Chem A. 2013;1(42):13120-7. Epub Sep. 13, 2013. Author manuscript, 25 pages.

Mao et al., Polyvinylferrocene for noncovalent dispersion and redox-controlled precipitation of carbon nanotubes in nonaqueous media. Langmuir. Aug. 6, 2013;29(31):9626-34. doi: 10.1021/la401440w. Epub Jun. 25, 2013.

Oren, Capacitive deionization (CDI) for desalination and water treatment—past, present and future (a review). Desalination. Aug. 15, 2008;228(1-3):10-29.

Pasta et al., A desalination battery. Nano Lett. Feb. 8, 2012;12(2):839-43. doi: 10.1021/nl203889e. Epub Jan. 23, 2012.

Porada et al., Direct prediction of the desalination performance of porous carbon electrodes for capacitive deionization. Energy Environ Sci. Aug. 2013;6(12):3700-12. Electronic Suppl Info, 21 pages.

Porada et al., Review on the science and technology of water desalination by capacitive deionization. Prog Mater Sci. Oct. 2013;58(8):1388-442. Epub Apr. 4, 2013.

Reis et al., Single-pot conversion of methane into acetic acid in the absence of CO and with vanadium catalysts such as amavadine. Angew Chem Int Ed Engl. Feb. 17, 2003;42(7):821-3.

Ren et al., Synthesis and solution self-assembly of side-chain cobaltocenium-containing block copolymers. J Am Chem Soc. Jul. 7, 2010;132(26):8874-5. Epub Jun. 14, 2010.

Reynes et al., Redox sensing of anions in pure aqueous environment by ferrocene-containing 4,4'-bipyridinium-based receptors and polymer films. Chem Commun. 2004;0:428-9.

Ruttiger et al., One for all: cobalt-containing polymethacrylates for magnetic ceramics, block copolymerization, unexpected electrochemistry, and stimuli-responsiveness. Polym Chem. 2016;7:1129-37. Epub Dec. 14, 2015.

Shannon et al., Science and technology for water purification in the coming decades. Nature. Mar. 20, 2008;452(7185):301-10. doi: 10.1038/nature06599.

Smyrl et al., Electrical and electrochemical properties of electronically conducting polymers. Ch. 2 in Applications of Electroactive Polymers. First Ed. Scrosati et al. (Ed). Springer Science and Business Media, BV. Jan. 2003. pp. 29-74.

Sola et al., Unprecedented 1,3-diaza[3]ferrocenophane scaffold as molecular probe for anions. Inorg Chem. May 2, 2011;50(9):4212-20. doi: 10.1021/ic102314r. Epub Feb. 14, 2011.

Su et al., Anion-selective redox electrodes: Electrochemically mediated separation with heterogeneous organometallic interfaces. Adv Funct Mater. May 2016;26(20):3394-404.

Su et al., Redox electrodes for selective electrochemical separations. Adv Coll Interf Sci. Jun. 2017;244:6-20. doi: 10.1016/m.cis.2016.09.001. Epub Sep. 9, 2016.

Subramani et al., Emerging desalination technologies for water treatment: A critical review. Water Res. May 15, 2015;75:164-87. doi: 10.1016/j.watres.2015.02.032. Epub Feb. 26, 2015.

Suss et al., Water desalination via capacitive deionization: what is it and what can we expect from it? Energy Environ Sci. 2015;8:2296-319. Epub May 5, 2015.

Takahashi et al., Electrochemical reduction of $CO_2$ at copper single crystal Cu(S)-[n(111)×(111)] and Cu(S)-[n(110)×(100)] electrodes. J Electroanal Chem. Sep. 20, 2002;533(1-2):135-43.

Teasdale et al., Molecular recognition using conducting polymers: Basis of an electrochemical sensing technology—Plenary lecture. Analyst. Apr. 1993;118:329-34.

Tian et al., Electrochemically nanostructured polyvinylferrocene/polypyrrole hybrids with synergy for energy storage. Adv Funct Mater. Aug. 2015;25(30):4803-13. Epub Jun. 24, 2015.

Tomapatanaget et al., Calix[4]arenes containing ferrocene amide as carboxylate anion receptors and sensors. Org Lett. May 1, 2003;59):1539-42.

Wang et al., Reversible multivalent (monovalent, divalent, trivalent) ion insertion in open framework and materials. Adv Energy Mater. 2015;5:1401869(1-10).

Yang et al., Metal-nucleic acid cages. Nat Chem. Aug. 2009;1(5):390-6. doi: 10.1038/nchem.290. Epub Jul. 24, 2009.

Zhang et al., Electrocatalytic reduction of carbon dioxide by cobalt-phthalocyanine-incorporated polypyrrole. Electrochem Solid-State Lett. 2009;12(8):E17-19. Epub May 19, 2009.

International Search Report and Written Opinion for Application No. PCT/US2017/058888 dated Feb. 28, 2018.

International Preliminary Report on Patentability for Application No. PCT/US2017/058888 dated May 9, 2019.

Tran et al., Incorporation of single-walled carbon nano tubes into ferrocene-modified linear polyethylenimine redox polymer films. Langmuir. May 17, 2011;27(10):6201-10. doi: 10.1021/la104999f. Epub Apr. 11, 2011.

Extended European Search Report for Application No. 16860821.4 dated Aug. 5, 2019.

Invitation to Pay Additional Fees for Application No. PCT/US2017/058888 dated Jan. 4, 2018.

\* cited by examiner

USE OF ELECTROCHEMICAL DEVICES OR SYSTEMS COMPRISING REDOX-FUNCTIONALIZED ELECTRODES FOR BIOSEPARATION AND BIOCATALYSIS

RELATED APPLICATIONS

This application is a national stage filing under 35 U.S.C. 0 371 of International Patent Application Serial No. PCT/US2017/058888, filed Oct. 27, 2017, and entitled "USE OF ELECTROCHEMICAL DEVICES OR SYSTEMS COMPRISING REDOX-FUNCTIONALIZED ELECTRODES FOR BIOSEPARATION AND/OR BIOCATALYSIS", which claims priority under 35 U.S.C. § 119(e) to U.S. Provisional Patent Application Ser. No. 62/413,960, filed Oct. 27, 2016, and entitled "USE OF ELECTROCHEMICAL DEVICES OR SYSTEMS COMPRISING REDOX-FUNCTIONALIZED ELECTRODES FOR BIOSEPARATION AND BIOCATALYSIS", the contents of which are incorporated by reference herein in their entirety.

TECHNICAL FIELD

Various aspects described herein relate to electrochemical devices, e.g., for separation of one or more biomolecules from a solution, and methods of using the same. Methods for using the electrochemical devices for biocatalysis are also described herein.

BACKGROUND

Bioseparation, e.g., protein separation, has been a primary challenge of biotechnology for the past decades, and with the advances of both functional materials as well as increasing demands in selectivity, there is a need to develop novel materials and methods for more efficient bioseparation, e.g., protein separation.

SUMMARY

The present disclosure is, in part, based on the design and construction of an electrochemical separation device with redox-functionalized electrode(s) tuned to selectively interact with a functional group of a target biomolecule during modulation of an electrical potential applied to the electrodes, thereby separating the target biomolecule from solution. As used herein, the term "biomolecule" refers to naturally occurring or synthetic (e.g., biomimetic) molecules including biomacromolecules. The biomolecule can be a charged molecule (e.g., a negatively charged molecule, a positively-charged molecule, a polar molecule), a neutral molecule, or a non-polar molecule. In some embodiments, the biomolecule has a weight average molecule weight of about 10 kDa to about 100 kDa. Examples of biomolecules include but are not limited to proteins, nucleic acid (e.g., DNA, RNA), viruses, bacteria, peptides, amino acid fragments, antibodies, enzymes, sugars, fatty acids, lipids, vitamins, co-enzymes, and combinations thereof.

In one example, a redox species (e.g., a metallocene such as ferrocene) that is selective toward a target electron donating functional group (e.g., a moiety that donates one or more electrons such as carboxylate) of a target biomolecule is immobilized to an anodic electrode. Upon application of an electrical potential, the redox species (e.g., a metallocene such as ferrocene) of the anodic electrode is oxidized, which captures target biomolecules through the target electron donating functional group (e.g., carboxylates) of the target biomolecules. In some embodiments where the redox species is a metallocene, the selectivity relies on the direct interaction (e.g., hydrogen bonding) of the target biomolecule with the cyclopentadienyl ring of the metallocene. The captured target biomolecules can be subsequently released or desorbed by reversal (partial or complete, including V=0) of the applied electrical potential, with minimal or no pH, temperature, or other changes in solution condition. The electrochemical devices or systems described herein do not rely on intercalated ions between a layered structure of an electrode that reversibly move from the electrode to another.

Accordingly, one aspect of the present disclosure features a method of separating a target biomolecule from a solution. The method comprises (a) contacting an aqueous solution with (i) a first electrode comprising a first substrate (e.g., a first solid substrate) and a first redox-species immobilized to the first substrate (e.g., a first solid substrate), wherein the first redox-species is selective toward a target functional group or a target functional site of a biomolecule based on a specific chemical interaction between the first redox species and the target functional group or a target functional site, wherein the specific chemical interaction is activated by a Faradaic/redox reaction; and (ii) a second electrode; and (b) applying an electrical potential across the first electrode and the second electrode such that the first redox species transforms from a first redox state to a second redox state and binds to the target functional group or the target functional site of a target biomolecule present in the solution, thereby separating the target biomolecule from the solution.

In some embodiments, the solution can further comprise one or more non-target biomolecules.

In some embodiments, the first electrode is an anodic electrode.

In some embodiments, the first electrode is a cathodic electrode.

Upon application of an electric potential, the first redox species transforms from a first redox state to a second redox state. Depending on the first redox state of the first redox species, in some embodiments, the first redox species may be oxidized to comprise an electron-receptor functional group (e.g., a moiety that accepts one or more electrons) upon application of an electrical potential, thereby selectively binds to an electron-donating functional group of a target biomolecule. In other embodiments, the first redox species may be reduced to a neutral redox state or a negatively-charged redox state, thereby selectively binds to a positively-charged group of a target biomolecule.

In some embodiments where the first redox species is oxidized upon application of an appropriate electrical potential, examples of such a first redox species include, but are not limited to organometallic compounds or polymers, an organic species or organic polymer, or a crystalline solid. An exemplary organometallic polymer includes, but is not limited to polyvinyl(ferrocene). Other first redox species, e.g., cyclodextrin-based systems, metal-polypyrridyl systems, metal dicarbamate, cryptand, redox-active arene, dendrimer comprising a redox-active center, and/or redox-active organic macrocycles, can also be used in the first electrodes.

In some embodiments involving the methods described herein, the first redox species present in the first electrode comprises a metallocene.

In some embodiments involving various first electrodes described herein, the first redox species or metallocene comprises a ferrocene-based redox species. In these embodiments, the cyclopentadienyl ligand of ferrocenium (oxidized state of ferrocene) can form a hydrogen bonding with a biomolecule comprising a carboxylate moiety or amino moiety.

In some embodiments involving various first electrodes described herein, the first redox species may interact with a target functional group or a target functional site comprising a hydrophobic domain, a hydrophilic domain, and/or a specific charge distribution or net charge.

In some embodiments where the first redox species is reduced (e.g., to a neutral state or a negatively-charged state) upon application of an appropriate electrical potential, examples of such a first redox species include, but are not limited to neutral or charged molecules comprising an electron-acceptor moiety. In some embodiments, the first redox species may be a charge species of the following compounds, which include but are not limited to organometallic compounds (e.g., but not limited to polyvinyl (ferrocene), cyclodextrin-based systems, metal-polypyrridyl systems, metal dicarbamate, cryptand, redox-active arene, dendrimer comprising a redox-active center, and/or redox-active organic macrocycles) or polymers, an organic species or organic polymer, or a crystalline solid.

In various embodiments involving the methods described herein, the second electrode can be electrically conductive and electrochemically inert; or a conductive electrode functionalized with a redox species. In some embodiments, the redox species in the second electrode can be (i) the same redox species as in the first electrode; (ii) a redox species with identical chemical identity to the redox species of the first electrode, but in a different oxidation state; or (iii) a redox species that has a different charge and chemical identity from that of the redox species of the first electrode. In some embodiments where the second electrode is redox-responsive, the second electrode can comprise a second substrate (e.g., a second solid substrate) and a second redox species immobilized to the second substrate (e.g., second solid substrate), wherein the second redox species undergoes a redox reaction during operation of the electrochemical system.

In some embodiments where the first electrode is an anodic electrode and the second electrode is a cathodic electrode, examples of the second redox species include, but are not limited to neutral or charged molecules comprising an electron-acceptor moiety; and charged species of the first redox species described herein.

In some embodiments where the first electrode is a cathodic electrode and the second electrode is an anodic electrode, examples of the second redox species include, but are not limited to organometallic compounds or polymers, an organic species or organic polymer, or a crystalline solid. An exemplary organometallic polymer includes, but is not limited to polyvinyl(ferrocene). Other second redox species, e.g., cyclodextrin-based systems, metal-polypyrridyl systems, metal dicarbamate, cryptand, redox-active arene, dendrimer comprising a redox-active center, and/or redox-active organic macrocycles, can also be used in the second electrodes.

Not only the electrochemical systems and/or methods described herein can be used for electrochemical bioseparation, they can also be used for redox-based sensing and/or electrocatalysis. Accordingly, another aspect described herein relates to a method of preparing an electrochemical system for biocatalysis or biosensing. The method comprises: (a) contacting an aqueous solution comprising an enzyme with (i) a first electrode comprising a substrate (e.g., a solid substrate) and a first redox-species immobilized to the substrate (e.g., solid substrate), wherein the first redox-species is selective toward a target functional group or a target functional site of the enzyme based on a specific chemical interaction between the first redox species and the target functional group, wherein the specific chemical interaction is activated by a Faradaic/redox reaction; and (ii) a second electrode; and (b) applying an electrical potential across the first electrode and the second electrode to activate the Faradaic/redox reaction such that the first redox species transforms from a first redox state to a second redox state and selectively binds to the target functional group or target functional site of the enzyme, wherein the enzyme remains stable during application of the electrical potential, thereby preparing an electrochemical system comprising the enzyme reversibly attached to the first electrode. In some embodiments, the first electrode is an anodic electrode. In some embodiments, the first electrode is a cathodic electrode.

A variety of enzymes classes can be used to prepare such an electrochemical system for biocatalysis or biosensing, including, for example, but not limited to oxidoreductases, transferases, hydrolases, lyases, aldolases, ketolases, hydratases, dehydratases, isomerases, ligases, and proteases. In some embodiments where the first electrode is an anodic electrode, enzymes that are amenable to the methods described herein are negatively-charged enzymes (e.g., enzymes with a negative net charge) or enzymes having at least one negatively-charged domain. In some embodiments where the first electrode is a cathodic electrode, enzymes that are amenable to the methods described herein are positively-charged enzymes (e.g., enzymes with a positive net charge) or enzymes having at least one positively-charged domain. Accordingly, various biocatalytic systems produced by such a method are also provided herein.

In a further aspect, the present disclosure provides a method comprising performing biocatalysis in any of the biocatalytic systems described herein, wherein an electrical potential is applied across the first electrode and the second electrode to activate the Faradaic/redox reaction such that the enzyme is reversibly attached to the first electrode and remains stable during application of the electrical potential.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the description of specific embodiments presented herein.

FIG. 3A shows chronoamperometry voltage and current profiles with 80 seconds, +0.4 V adsorption, fixed 0 V self-discharge for desorption. FIG. 3B shows FPLC profiles for BSA and MYO of adsorption stock (1 mg/mL BSA, MYO each) and desorption supernatant (after electrosorption and release using PVF/CNT) analyzed through a size exclusion column, normalized based by MYO peak.

DETAILED DESCRIPTION OF EXEMPLARY EMBODIMENTS

Figure 1A:
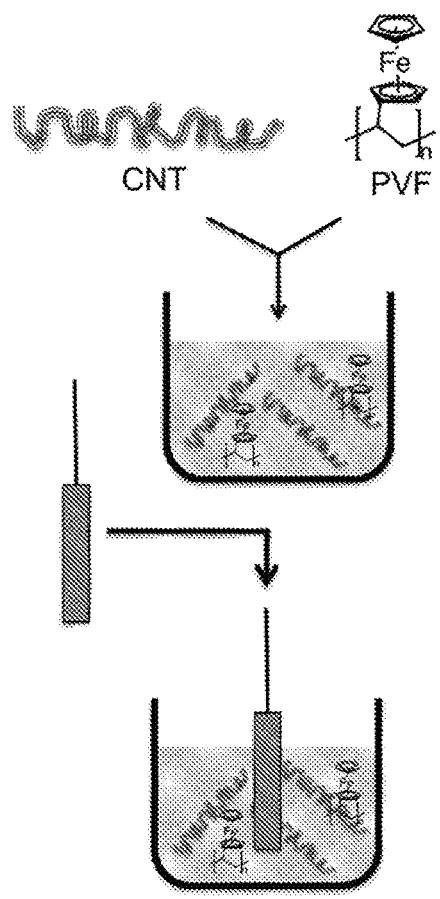
FIG. 1A shows the electrode preparation method for dip-coated PVF-CNT.

Selective recovery or separation of diluted biomolecules from solution is a crucial challenge in the pharmaceutical industries or bioseparation industries. Accordingly, there is a need to develop efficient, affordable and robust bioseparation technologies.

The present disclosure is, in part, based on the design and construction of an electrochemical separation device that utilized redox-functionalized electrode(s) to selectively remove one or more target biomolecules (including biomacromolecules, e.g., with a molecular weight of up to 100 kDa or higher) from solution by modulating the electrical potential applied to the device. For example, adsorption or capture of one or more target biomolecules to redox-functionalized electrodes depends on the changes in the redox state of the redox species within the electrodes when an electrical potential is applied, while release of the captured species relies on reversal of the applied electrical potential, with minimal or no pH, temperature, or other changes in solution conditions. The electrochemical devices or systems described herein do not rely on intercalated ions between a layered structure of an electrode that reversibly move from the electrode to another.

High selectivity for target biomolecules is achieved, at least in part, by functionalizing at least one electrode (e.g., anode and/or cathode) with a redox species that is tuned to selectively interact with a certain functional group or functional site of a target biomolecule, wherein the chemical interaction between the redox species and the functional group is activated by a Faradaic/redox reaction. In some embodiments, both electrodes (e.g., anode and cathode) each can be functionalized with a redox species that is tuned to interact with a specific functional group or functional site of different target biomolecules. For example, the inventors have discovered a specific type of redox-activated chemical interaction (e.g., a redox-activated directional hydrogen bonding) between the cyclopentadienyls of a metallocene-based system (e.g., ferrocene-based system) and carboxylate group of a target biomolecule (including biomacromolecule) when the metallocene is oxidized. Such specific redox-activated chemical interaction between the electrode (e.g., anode and/or cathode) and the target biomolecule (including biomacromolecule) allows for recognition and separation of at least one target biomolecule from other competing species such as other competing biomolecules in an aqueous phase. Thus, such separation of biomolecules is not merely based on size or charge of the biomolecules as employed by the conventional separation methods, but rather relies on the specific interaction between the electrode redox species and the target biomolecule(s) to be separated. The discovery described herein can be extended to design of other metallocenes and functionalized redox-species using specific chemical interaction for more efficient electrochemical separation and/or biocatalysis.

Accordingly, aspects of the present disclosure feature electrochemical devices or systems each comprising at least one redox-functionalized electrode that is selective toward a target biomolecule, as well as methods of separating at least one target biomolecule from a solution. As used herein, an "electrochemical system" is a system that is configured to provide an electrical potential across electrodes to induce one or more chemical reactions at the electrodes. "Electrochemical reactions" are those reactions within the electrochemical system that, directly or indirectly, produce or consume electrons. Upon application of an electrical potential, electrons generated by a voltage generator, e.g., can be transferred between an anode and a cathode. Generally, the electrochemical reactions will include at least one oxidation reaction and at least one reduction reaction. In most cases, the oxidation electrochemical reaction generates electrons, and the reduction electrochemical reaction consumes electrons.

Generally, an "electrode" corresponds to a solid material within the electrochemical system at which a reduction or oxidation reaction occur. The anode is the electrode at which oxidation occurs during application of an electrical potential, and the cathode is the electrode at which reduction occurs during application of an electrical potential.

The electrochemical system may also include, according to certain embodiments, other optional components such as, for example, an electrolyte (e.g., a liquid electrolyte which may, for example, facilitate the transport of ions between the electrodes of the electrochemical system during operation), a vessel (e.g., any suitable container), external electrical connections, and the like.

Methods for Bioseparation and/or Catalysis

One aspect of the present disclosure features a method of separating a target biomolecule from a solution. The method comprises (a) providing an electrochemical system comprising (i) a first electrode comprising a first substrate (e.g., a first solid substrate) and a first redox-species immobilized to the first substrate (e.g., the first solid substrate), wherein the first redox-species is selective toward a target functional group or a target functional site of a biomolecule based on a specific chemical interaction between the first redox species and the functional group or a target functional site, wherein the specific chemical interaction is activated by a Faradaic/redox reaction; and (ii) a second electrode, wherein the first electrode and the second electrode are in contact with an electrolyte; and (b) applying an electrical potential across the first electrode and the second electrode such that the first redox species transforms from a first redox state to a second redox state and selectively binds to the target functional group of the target biomolecule present in the solution, thereby separating the target biomolecule from the solution.

In some embodiments, the target biomolecule is a molecule that shares a carbon backbone. In some embodiments, the target biomolecule may comprise proteins, nucleic acids or polynucleotides (e.g., DNA, RNA, genetic materials), carbohydrates, disaccharides, polysaccharides, viruses, bacteria, peptides, amino acid fragments, antibodies, enzymes, sugars, fatty acids, lipids, vitamins, co-enzymes, and combinations thereof. The target biomolecule can be naturally occurring or synthetic (e.g., biomimetic). In some embodiments, the biomolecule is a naturally occurring or synthetic (e.g., biomimetic) biomacromolecule (with large molecular weight). In some embodiments, the target biomolecule may be obtained or derived from a biological source, including, e.g., but not limited to cells, tissues, organisms, and bodily fluids (e.g., blood, serum, or urine).

In some embodiments, the target biomolecule may be a monomer, which is the building block of a biomolecule. Examples of such monomers include, but are not limited to, amino acids, monosaccharides, fatty acids, and nucleotides.

In some embodiments, the target biomolecule may be a biopolymer comprising a plurality of (e.g., at least 2 or more, including, e.g., at least 5, at least 10, at least 25, at least 50, at least 75, at least 100, at least 200, at least 300, at least 400, at least 500, at least 600, at least 700, at least 800, at least 900, at least 1000, or more) monomers (including, e.g., but not limited to amino acids, monosaccharides, fatty acids, and nucleotides) joined by covalent bonds. For example, a peptide or protein is a biopolymer comprising a plurality of amino acids joined by peptide bonds.

In some embodiments, the target biomolecule has a molecule weight of at least 1 kDa, at least 2 kDa, at least 3 kDa, at least 4 kDa, at least 5 kDa, at least 10 kDa, at least 20 kDa, at least 30 kDa, at least 40 kDa, at least 50 kDa, at least 60 kDa, at least 70 kDa, at least 80 kDa, at least 90 kDa, at least 100 kDa, at least 200 kDa, at least 300 kDa, at least 400 kDa, or at least 500 kDa. In some embodiments, the target biomolecule has molecule weight of no more than 500 kDa, no more than 400 kDa, no more than 300 kDa, no more than 200 kDa, no more than 100 kDa, no more than 90 kDa, no more than 80 kDa, no more than 70 kDa, no more than 60 kDa, no more than 50 kDa, no more than 40 kDa, no more than 30 kDa, no more than 20 kDa, or no more than 10 kDa. Combinations of the above-referenced ranges are possible. For example, in some embodiments, the target biomolecule may have a molecular weight of about 10 kDa to about 100 kDa. In other embodiments, the target biomolecule may have a molecular weight of about 5 kDa to about 500 kDa. Other combinations are also possible. The molecular weights of the target biomolecule described herein can correspond to weight average molecular weights, number average molecular weights, or peak average molecular weights. The average molecular weights of the target biomolecule can be determined by any known methods in the art, including, e.g., but not limited to, gel electrophoresis (e.g., sodium dodecyl sulfate polyacrylamide gel electrophoresis (SDS-PAGE), size exclusion gel chromatography, mass spectroscopy (e.g., MALDI or ESI), or high performance liquid chromatography (HPLC), refractive index detection, light scattering, or any combinations thereof.

In some embodiments, the target biomolecule has an internal dipole moment of at least 50 Debye, at least 75 Debye, at least 100 Debye, at least 150 Debye, at least 200 Debye, at least 300 Debye, at least 400 Debye, at least 500 Debye, at least 600 Debye, at least 700 Debye, at least 800 Debye, at least 900 Debye, or at least 1000 Debye. In some embodiments, the target biomolecule has an internal dipole moment of no more than 1500 Debye, no more than 1400 Debye, no more than 1300 Debye, no more than 1200 Debye, no more than 1000 Debye, no more than 900 Debye, no more than 800 Debye, no more than 700 Debye, no more than 600 Debye, no more than 500 Debye, no more than 400 Debye, no more than 300 Debye, no more than 200 Debye, or no more than 100 Debye. Combinations of the above-referenced ranges are possible. For example, in some embodiments, the target biomolecule may have an internal dipole moment of about 100 Debye to about 1000 Debye. Other combinations are also possible. The internal dipole moment for a target biomolecule can be determined from literature or as calculated from molecular dynamics simulations. For example, the internal dipole moments can be calculated from the Protein Dipole Moments Server, which is accessible at dipole/weizmann.ac.il/, based on the target biomolecule's PDB file.

In some embodiments, the target biomolecule may have no net charge over the entire molecule (referred to herein as a "neutrally-charged" biomolecule). For example, a neutrally-charged biomolecule may have at least one positively-charged domain and at least one negatively-charged domain, resulting in a net charge of zero. In these embodiments, a neutrally-charged biomolecule may bind to an anodic electrode or a cathodic electrode depending on the design of redox reactions and electrodes. For example, in some embodiments where an anodic electrode is functionalized with a redox-species that is selective toward a negatively-charged domain of a target biomolecule, the target biomolecule preferentially binds to the anodic electrode based on the interaction of the redox species and the negatively-charged domain of the target biomolecule. In some embodiments where a cathodic electrode is functionalized with a redox-species that is selective toward a positively-charged domain of a target biomolecule, the target biomolecule preferentially binds to the cathodic electrode based on the interaction of the redox species and the positively-charged domain of the target biomolecule.

In some embodiments, the target biomolecule may have a positive net charge over the entire molecule (referred to herein as a "positively-charged" biomolecule). A target biomolecule with a positive net charge may preferentially bind to a cathode with a redox species tuned to a target functional group of the target biomolecule.

In some embodiments, the target biomolecule may have a negative net charge over the entire molecule (referred to herein as a "negatively-charged" biomolecule). A target biomolecule with a negative net charge may preferentially bind to an anode with a redox species tuned to a target functional group of the target biomolecule.

In some embodiments, electrochemical devices or systems that can be used to separate a target biomolecule comprise (i) a first electrode comprising a first substrate (e.g., a first solid substrate) and a first redox-species immobilized to the first substrate (e.g., the first solid substrate), wherein the first redox-species is selective toward a target functional group or a target functional site of a biomolecule based on a specific chemical interaction between the first redox species and the functional group or a target functional site, wherein the specific chemical interaction is activated by a Faradaic/redox reaction; and (ii) a second electrode, wherein the first electrode and the second electrode are in contact with an electrolyte.

As used herein, the term "immobilized" refers to a redox species that is coupled, directly or indirectly, to an electrode is not able to move freely from one electrode to another electrode. The term "coupled" as used herein means to chemically associate one entity (for example a moiety) with another. In some embodiments, the coupling is covalent. For example, metallocene is covalently attached to a polymer such as polyvinyl(ferrocene). In non-covalent embodiments, the non-covalent coupling is mediated by non-covalent interactions including but not limited to charge interactions, affinity interactions, metal coordination, physical adsorption, hydrophobic interactions, hydrogen bonding interactions, van der Waals interactions, dipole-dipole interactions, and/or combinations thereof. In some embodiments, the coupling is encapsulation.

Upon application of an electrical potential, the first redox species transforms from a first redox state to a second redox state and selectively binds to a target functional group of a target biomolecule. For example, the first redox species in a certain redox state is selective toward a target functional group (e.g., a target molecular moiety) when it has a higher binding affinity for the target functional group or the target functional site than for a non-target species, e.g., by at least about 1.1-fold, at least about 1.5-fold, at least about 2-fold, at least about 3-fold, at least about 4-fold, at least about 5-fold, at least about 10-fold, at least about 25-fold, at least about 50-fold, at least about 100-fold, at least about 200-fold, at least about 300-fold, at least about 400-fold, at least about 500-fold, at least about 1000-fold or more. Alternatively, the first redox species in a certain redox state is selective toward a target functional group (e.g., a target molecular moiety) when a separation factor of a target biomolecule comprising the target functional group (relative to a non-target species) is at least 5 or more, including, e.g., at least 10, at least 20, at least 30, at least 40, at least 50, at least 60, at least 70, at least 80, at least 90, at least 100, at least 125, at least 150, at least 175, at least 200, at least 250, at least 300, at least 350, at least 400, at least 450, at least 500, or more.

As used herein, the term "redox species" generally refers to any molecule or compound or a portion thereof (e.g., a molecular or functional moiety of a molecular or compound) that can be oxidized and/or reduced during or upon electrical stimulation (e.g., during or upon application of an electrical potential), or can undergo a Faradaic reaction. For example, a redox species comprises one or more molecular moieties that accept and/or donate one or more electrons depending on its redox state. Thus, the redox species can form part (e.g., a molecular moiety) of a small molecule, a compound, a polymer molecule, or can exist as an individual molecule or compound.

Depending on the first redox state of the first redox species, in some embodiments, the first redox species may be oxidized to comprise an electron-receptor functional group (e.g., a moiety that accepts one or more electrons) upon application of an appropriate electrical potential, thereby selectively binds to an electron-donating functional group of a target biomolecule. In other embodiments, the first redox species may be reduced to a neutral redox state or a negatively-charged redox state, thereby selectively binds to a positively-charged group of a target biomolecule. Accordingly, in some embodiments, the target functional group of a target biomolecule can comprise a carboxylate moiety or amino moiety. In some embodiments, the specific chemical interaction between the first redox species and the target functional group (or a target functional site) may be based on charge distribution, hydrophobic interactions, and/or hydrophilic interactions.

In some embodiments of various first electrodes described herein, the first redox species can be oxidized to form a species that comprises an electron-receptor moiety upon application of an appropriate electrical potential. Examples of such a first redox species include, but are not limited to organometallic compounds or polymers, an organic species (e.g., polymers), or a crystalline solid. An organometallic compound is generally a compound comprising at least one metal-carbon (M-C) bond where the carbon is part of an organic group. Examples of such organic group include, but are not limited to, alkyl (e.g., methyl), alkylidene (e.g., carbene), alkene (e.g., ethene), allyl (e.g., $-C_3H_5$), alkylidyne (e.g., carbyne), 1,3-butadiene (e.g., $C_4H_6$), cyclobutadiene (e.g., $C_4H_4$), cyclopentadienyl ($C_5H_5$), benzene (e.g., $C_6H_6$), and cyclooctatetraene (e.g., $C_8H_8$). The metal in the metal-carbon (M-C) bond of organometallic compounds include metals (e.g., Li, Mg, and Al), metalloids, and transition metals (e.g., Fe, Co, Cr, and Ni). Organometallic compounds include, among others, metallocenes, polymers and derivatives, metal-bipyiridine systems, ferricyanide type systems, porphyrins, phthalocyanines, and pincer-ligand metal systems. An organometallic polymer is a polymer comprising an organometallic compound, e.g., a polymer comprising metallocene. An exemplary organometallic polymer includes, but is not limited to polyvinyl(ferrocene).

Additional non-limiting examples of the first redox species that can be used in various first electrodes include polymeric redox-systems, e.g., polyaniline-type systems, polypyrrole, polythiophene, and their derivatives; crystalline solids, e.g., redox-active metal-based nanoparticles, redox-active heteropolyacids, redox-active metal-organic frameworks, redox-active crystalline polymer frameworks (e.g., covalent-organic frameworks); cyclodextrin-based systems, metal-polypyridyl systems, metal-dicarbamates, cryptands, redox-active arenes, dendrimers comprising redox-active centers, and redox-active organic macrocycles.

In some embodiments, the first redox species present in the first electrode (e.g., anode) comprises a metallocene. A metallocene is a compound comprising two cyclopentadienyl rings and a metal center coordinated in a sandwich structure, wherein the metal center is oxidized to form a metal ion upon electrical stimulation. Thus, in another aspect, the present disclosure provides a method using an electrochemical device or system comprising a first electrode that comprises a metallocene-comprising substrate (e.g., a metallocene-comprising solid substrate), wherein the metallocene is selective toward a target functional group or a target functional site of a target biomolecule and a second electrode (e.g., cathode), to separate the target biomolecule from the solution.

In some embodiments of various first electrodes described herein, the first redox species or metallocene comprises a ferrocene-based redox species. In some embodiments, the cyclopentadienyl ligand or ring of ferrocenium (oxidized state of ferrocene) can form a hydrogen bonding with a target functional group or a target functional site of a target biomolecule. In some embodiments, the target functional group or target functional site may comprise a carboxylate moiety or amino moiety. In some embodiments involving various first electrodes described herein, the first redox species may interact with a target functional group comprising a hydrophobic domain, a hydrophilic domain, and/or a specific charge distribution. Accordingly, different embodiments of the electrochemical devices or systems and methods described herein can be tuned to separate target biomolecules from other competing species (e.g., dissolved target biomolecules) in the solution based on different characteristics, e.g., but not limited to size, isoelectric points, charge distribution, hydrophobicity, hydrophilicity, and combinations hereof.

For example, the selectivity of metallocene-based electrodes for a target biomolecule can be enhanced through tuning of composition of an electrolyte, and/or modification of the metallocene rings, e.g., by adding electron withdrawing and/or electron donating functional groups to modulate the strength of the cyclopentadienyl hydrogen bonding. See, e.g., the International Patent Application No. PCT/US2016/059193 entitled "Electrochemical Devices or Systems Comprising Redox-Functionalized Electrodes and Uses Thereof" filed Oct. 27, 2016, the content of which is incorporated herein by reference in its entirety, for additional information on tuning selectivity of metallocene-based electrodes.

In some embodiments of various first electrodes described herein, the first redox species can be reduced to form a species that comprises an electron-donating moiety upon application of an appropriate electrical potential. Examples of such first redox species include, but are not limited to neutral or charged molecules comprising an electron-acceptor moiety. In some embodiments, the first redox species may be a charge species of the following compounds, which include but are not limited to organometallic compounds (e.g., but not limited to polyvinyl(ferrocene), cyclodextrin-based systems, metal-polypyrridyl systems, metal dicarbamate, cryptand, redox-active arene, dendrimer comprising a redox-active center, and/or redox-active organic macrocycles) or polymers, an organic species or organic polymer, or a crystalline solid.

In some embodiments involving the methods and/or electrochemical systems of any aspects described herein, the first electrode contains the first redox species (e.g., as described herein) in an amount of greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, or greater than or equal to 90 wt %. In certain embodiments, the first electrode contains the first redox species (e.g., as described herein) in an amount of less than or equal to 100 wt %, less than or equal to 99 wt %, less than or equal to 95 wt %, less than or equal to 90 wt %, less than or equal to 80 wt %, less than or equal to 70 wt %, or less than or equal to 60 wt %. Combinations of the above-referenced ranges are also possible (e.g., greater than or equal to 20 wt % and less than or equal to 100 wt %). Other ranges are also possible.

In some embodiments involving the methods and/or electrochemical systems of any aspects described herein, the first electrode contains the substrate (e.g., solid substrate) and the first redox species (e.g., described herein) in an amount as described above, wherein the first redox species is dispersed in the substrate (e.g., solid substrate) and is stabilized through non-covalent interactions (e.g., $\pi$-$\pi$ interactions) with the substrate (e.g., solid substrate).

In some embodiments involving the methods and/or electrochemical systems of any aspects described herein, the second electrode can have a conductive surface such as porous carbon, metal, composite, inorganic or organic polymer, which can be redox-responsive or redox-non-responsive. For example, the second electrode can be electrically conductive and electrochemically inert (e.g., carbon, and/or platinum); or a conductive electrode functionalized with a redox species. In some embodiments, the redox species in the second electrode can be (i) the same redox species as in the first electrode; (ii) a redox species with identical chemical identity to the redox species of the first electrode, but in a different oxidation state; or (iii) a redox species that has a different charge and chemical identity from that of the redox species of the first electrode.

In some embodiments involving the methods and/or electrochemical systems of any aspects described herein, the second redox species can be a molecule, compound, or polymer comprising an electron-acceptor moiety, e.g., with a more favorable reduction process than water or solvent electrolysis (e.g., the redox potential for the second redox species lies above the water-reduction potential). The molecule, compound, or polymer comprising an elector-acceptor moiety can be a charged species or a neutral species. For example, a charged redox species can comprise a charged organometallic compound, which becomes neutrally charged upon reduction. In some embodiments, the charged organometallic compound can be a metallocenium-based species, e.g., but not limited to cobaltocenium-based redox species (e.g., cobaltocenium hexafluorphosphate or cobaltocenium-containing polymer such as poly(2-(methacryloly-oxy)ethyl cobaltocenium)). Other charged organometallic compounds that can be used to functionalize the second electrode include, but are not limited to, ruthenium-based redox species (e.g., cis-dichlorobis(2,2'-bipyridine)ruthenium(II)-based molecules or -containing polymer, or ferrocenium-based redox species. Alternatively, the second redox species can be a neutral molecule, compound, or polymer comprising an electron-acceptor moiety that becomes negatively charged upon reduction. Exemplary neutral redox species includes organic conducting polymers comprising electron-acceptor moieties, e.g., poly(anthraquinone), or ferricyanide-based redox species (e.g., complexes of ferricyanide such as potassium ferricyanide).

In some embodiments involving the methods and/or electrochemical systems of any aspects described herein, the second redox species can be a charged species of the first redox species described herein, which is reduction favorable. Non-limiting examples of such first species that can be used to form a charged species include quinone containing polymers (e.g., polyanthraquinone), Cobaltocenium containing polymers (e.g., poly(2-(methacrylolyoxy)ethyl cobaltocenium), and polypyrrole, as well as other possible redox-active species including, e.g., cyclodextrin-based systems, metal-polypyrridyl systems, metal-dicarbamates, cryptands, dendrimers comprising redox-active centers, and redox-active organic macrocycles.

In some embodiments involving the methods and/or electrochemical systems of any aspects described herein, the second redox species can comprise an organometallic compound or polymer, an organic species or organic polymer, and/or a crystalline solid. An exemplary organometallic polymer includes, but is not limited to polyvinyl(ferrocene). Other second redox species, e.g., cyclodextrin-based systems, metal-polypyrridyl systems, metal dicarbamate, cryptand, redox-active arene, dendrimer comprising a redox-active center, and/or redox-active organic macrocycles, can also be used in the second electrodes.

In some embodiments involving the methods and/or electrochemical systems of any aspects described herein, it may be desirable to have the second redox species of the second electrode chemically different from the first redox species of the first electrode to form an asymmetric redox-based electrochemical device or system. Asymmetric redox-based electrochemical devices or systems enable efficient separation of a diluted target species from a complex background (e.g., the presence of competing target biomolecules at a concentration that is at least 100-fold higher than that of the target species) with substantially constant pH over a wide range of current densities at a high current efficiency. In some embodiments, the current densities can range from about 0.5 $A/cm^2$ to about 10 $A/cm^2$, or about 0.8 $A/cm^2$ to about 8 $A/cm^2$. In some embodiments, the current efficiency can be at least about 90% or higher, including, e.g., at least about 95%, at least about 96%, at least about 97%, at least about 98%, or higher.

In some embodiments involving the methods and/or electrochemical systems of any aspects described herein, the second electrode contains the second redox species (e.g., as described herein) in an amount of greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, or greater than or equal to 90 wt %. In certain embodiments, the second electrode contains the second redox species (e.g., as described herein) in an amount of less than or equal to 100 wt %, less than or equal to 99 wt %, less than or equal to 95 wt %, less than or equal to 90 wt %, less than or equal to 80 wt %, less than or equal to 70 wt %, or less than or equal to 60 wt %. Combinations of the above-referenced ranges are also possible (e.g., greater than or equal to 20 wt % and less than or equal to 100 wt %). Other ranges are also possible.

In some embodiments involving the methods and/or electrochemical systems of any aspects described herein, the substrate (e.g., solid substrate) forming the electrodes can be porous, e.g., the substrate (e.g., solid substrate) comprising pores. As used herein, a "pore" generally refers to a conduit, void, or passageway, at least a portion of which is surrounded by a medium in which the pore is formed such that a continuous loop may be drawn around the pore while remaining within the medium. "Externally-accessible pores" are pores within the porous medium that are not completely surrounded by the solid material from which the porous medium is made, and thus, are accessible from outside the solid material from which the porous medium is made by a fluid (e.g., a liquid, gas, and/or supercritical fluid). The externally-accessible pores may be, according to certain embodiments, accessible by an electrolyte of the electrochemical system. Voids within a material that are completely surrounded by the solid material from which the porous medium is formed (and thus, not accessible from outside the porous medium, e.g. closed cells) are not externally-accessible pores. Pores may comprise any suitable cross-sectional shape such as, for example, circular, elliptical, polygonal (e.g., rectangular, triangular, etc.), irregular, and the like. The porous structure provides facile ion diffusion and high externally-accessible surface area of the pores that can be contacted by an external fluid (e.g., the electrolyte during operation of the electrochemical system).

Any art-recognized electrode material can be used in the substrate (e.g., solid substrate) to form the first and/or second electrodes described herein. In general, the substrate (e.g., solid substrate) can comprise one or more electrical conducting materials, e.g., but not limited to copper, carbon nanotubes, carbon paste, graphite, graphene, titanium, brass, silver, platinum, gold, ceramic material, and combinations thereof. The substrate (e.g., solid substrate) can be in the form of a layer, a mesh, a film, or a plate. In one embodiment, the substrate (e.g., solid substrate) for use in the electrodes of the electrochemical devices or systems described herein comprise a network of carbon nanotubes.

During operation of the electrochemical system described herein, the first and second electrodes are in contact with a fluid electrolyte (e.g., a liquid and/or supercritical fluid electrolyte). In some embodiments, the first and/or second electrodes are in contact with a liquid electrolyte. Generally, the electrolyte is capable of conducting ions but is not capable of conducting a sufficient amount of electricity to result in a short circuit of the electrochemical system. The pH of the electrolyte can be neutral, acidic, or basic. In some embodiments, the pH of the electrolyte can range from pH 1 to about pH 14. In some embodiments, the electrolyte has a pH that is above the isoelectric point of the target molecule (e.g., organic or inorganic molecules) for anion-selective separation. In some embodiments, the electrolyte has a pH that is below the isoelectric point of a cation species (e.g., organic or inorganic species) to be separated for cation-selective separation.

In some embodiments, the pH of the electrolyte can vary during the operation of the electrochemical systems described herein. In some embodiments, the pH of the electrolyte is substantially the same (e.g., within 10%, within 5%, or less) during the operation of the electrochemical systems described herein.

Generally, as noted above, the electrolyte serves as a medium for the transport of ions between the anode and the cathode. According to certain embodiments, the electrolyte may comprise one or more dissolved species or target biomolecules (e.g., inorganic or organic molecules) to be separated. In some embodiments, the electrolyte may comprise one or more dissolved salts. The salt may, according to certain embodiments, act as a pH buffer in the electrochemical system. The electrolyte may also contain, according to certain embodiments, one or more byproducts of the electrochemical reaction(s) employed by the electrochemical system.

In some embodiments, the electrolyte is an aqueous electrolyte. In some such embodiments, the electrolyte contains water in an amount of at least 50 wt %, at least 75 wt %, at least 90 wt %, or more.

In some embodiments, the electrolyte is an organic solvent electrolyte. In some such embodiments, the electrolyte contains organic solvent in an amount of at least 50 wt %, at least 75 wt %, at least 90 wt %, or more.

In certain embodiments, the electrochemical system may comprise additional components. For example, the electrochemical system may further comprise, according to certain embodiments, electrical contact pads and/or electrical leads (which can be connected to, for example, an external electrical potential generator, e.g., a voltage generator).

Other non-limiting examples of additional components include pumps, valves, storage tanks, flow meters, and mixers. In some embodiments, the electrochemical system may comprise a pump which is fluidically connected to the electrolyte. In certain embodiments, the electrochemical system may comprise a valve which is capable of allowing any gases or supercritical fluids generated during electrochemical system operation (e.g., hydrogen) to escape. In some embodiments, the electrochemical system may comprise a valve which is capable of allowing water and/or seawater into the chamber, in which the electrodes are placed. Additionally, in some embodiments, additional components such as structures, supports, and non-conductive separators may be present.

In some embodiments, the electrochemical system used in the methods described herein can comprise more than one set (e.g., 2 sets or more, 3 sets or more, 4 sets or more, 5 sets or more, 10 sets or more, or 20 sets or more) of the first and second electrodes arranged in series or in parallel. In some embodiments where the first and second electrodes are asymmetric (e.g., when the first and second electrodes have chemically different redox species, e.g., redox species having different chemical molecular structures), the electrodes can be arranged in series.

In some embodiments involving the methods and/or electrochemical systems of any aspects described herein, the second electrode can comprise a second substrate (e.g., solid substrate) and a second redox species immobilized to the second substrate (e.g., second solid substrate), wherein the second redox species is chemically different from the first redox species, e.g., the second redox species has a different chemical molecular structure from that of the first redox species.

In some embodiments involving the methods and/or electrochemical systems of any aspects described herein, the second electrode can be tuned to selectively capture a target ionic species present in the fluid source. In some embodiments where the second electrode is a cathodic electrode, the second electrode can be tuned to selectively capture a target cationic species present in the fluid source. In some embodiments where the second electrode is an anodic electrode, the second electrode can be tuned to selectively capture a target anionic species present in the fluid source. The target ionic species (e.g., cationic or anionic) species may be, for example, a positively-charged biomolecule selected from the group consisting of proteins, nucleic acids or polynucleotides, DNA, RNA, viruses, peptides, amino acid fragments, antibodies, enzymes, sugars, carbohydrates, fatty acids, lipids, vitamins, co-enzymes, peptides, and combinations thereof.

In some embodiments involving the methods and/or electrochemical systems of any aspects described herein, the second electrode can be tuned to selectively capture a target cationic species present in the fluid source, in the presence of competing alkali or alkaline earth metal cations (e.g., sodium and magnesium). For example, the second electrode can comprise a second redox species that is selective toward a target cation based on a specific chemical interaction between the second redox species and the target cation, wherein the specific chemical interaction between the second redox species and the target cation is activated by a Faradaic/redox reaction. Examples of such target cationic species include, but are not limited to transition metals and heavy metals such as chromium, lead, copper, zirconium, mercury, cadmium, zinc, nickel, aluminum, and tin; lanthanides, organic cations such as pyrridinium, and compounds with charged amino-groups. Metal-organic cations such as methylmercury and other organic mercury conjugates can also be separated using the electrochemical devices or systems and/or methods described herein. Selectivity has also been seen towards main-group cations (Group 1 and 2) such as lithium, sodium, potassium, among others. Rare-earth metals, e.g., scandium, yttrium, lanthanum, cerium, gandolinium, erbium, holmium, samarium, europium, terbium, dysprosium, thulium, and lutetium, tantalium and hafnium, can also be extracted using the electrochemical devices or systems and/or methods described herein. Valuable metals such as gold, silver, copper, ruthenium, iridium in charged forms can also be recovered using the electrochemical devices or systems and/or methods described herein.

In some embodiments involving the methods and/or electrochemical systems of any aspects described herein, the target biomolecule is present in a fluid source in a micromolar range or in a nanomolar range. In some embodiments, the target biomolecule is present at a micromolar concentration. For example, the target biomolecule is present in a solution or a sample at a concentration of about 0.1 micromolar, about 0.5 micromolar, about 1 micromolar, about 5 micromolar, about 10 micromolar, about 20 micromolar, about 30 micromolar, about 40 micromolar, about 50 micromolar, about 60 micromolar, about 70 micromolar, about 80 micromolar, about 90 micromolar, about 100 micromolar, about 200 micromolar, or more. Combinations of the above-referenced ranges are also possible. For example, in some embodiments, the target biomolecule may be present in a solution or a sample at a concentration of about 0.5 micromolar to about 100 micromolar, about 0.5 micromolar to about 50 micromolar, or about 0.5 micromolar to about 25 micromolar.

In some embodiments, the target biomolecule is present at a nanomolar concentration. For example, the target biomolecule is present in a solution or a sample at a concentration of about 0.01 nM, about 0.05 nM, about 0.1 nM, about 0.5 nM, about 1 nM, about 5 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, or more. Combinations of the above-referenced ranges are also possible. For example, in some embodiments, the target biomolecule may be present in a solution or a sample at a concentration of about 0.01 nM to about 1000 nM, or about 0.1 nM to about 500 nM, or about 1 nM to about 500 nM.

In some embodiments, the target biomolecule is present in a solution or a sample at a concentration of about 50 µg/mL to about 5000 mg/mL. Lower or higher concentrations are also possible. In some embodiments, the target biomolecule is present at a concentration of about 1 µg/mL, about 5 µg/mL, about 10 µg/mL, about 25 µg/mL, about 50 µg/mL, about 75 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, or about 1000 µg/mL. In some embodiments, the target biomolecule is present at a concentration of about 1 mg/mL, about 5 mg/mL, about 10 mg/mL, about 25 mg/mL, about 50 mg/mL, about 75 mg/mL, about 100 mg/mL, about 200 mg/mL, about 300 mg/mL, about 400 mg/mL, about 500 mg/mL, about 600 mg/mL, about 700 mg/mL, about 800 mg/mL, about 900 mg/mL, about 1000 mg/mL, about 2000 mg/mL, about 3000 mg/mL, about 4000 mg/mL, or about 5000 mg/mL. Other combinations of the above-referenced ranges are possible. For example, in some embodiments, the target biomolecule is present in a solution or a sample at a concentration of about 50 µg/mL to about 500 µg/mL, or about 25 µg/mL to about 200 µg/mL, or about 1 µg/mL to about 100 µg/mL.

In some embodiments, the solution can comprise other competing non-target species present at a concentration that is significantly higher (e.g., at least 5-fold or higher, including, e.g., at least 10-fold, at least 25-fold, at least 50-fold, at least 100-fold, at least 200-fold, at least 300-fold, at least 400-fold, at least 500-fold) than that of the target biomolecules.

The electrochemical systems and/or the methods described herein may be operated at a variety of suitable temperatures. In certain embodiments, the electrochemical system and/or the method is operated at a temperature such that the electrolyte remains in liquid and/or supercritical fluid form. In certain embodiments, the electrochemical system and/or the method is operated at a temperature such that the electrolyte remains in liquid form. For example, in certain embodiments, the electrochemical system and/or method may be operated at any temperature between 0° C. and 100° C. (e.g., at about 10° C., about 15° C., about 20° C., about 25° C., about 30° C., about 35° C., about 40° C., about 45° C., or higher) when under atmospheric pressure (e.g., 1 atm) or greater (e.g., at the increased pressure imposed by hydrostatic pressure underwater).

The electrochemical systems and/or the methods described herein may be operated at a variety of suitable pressures. In certain embodiments, the electrochemical system and/or method is operated at a pressure such that the electrolyte remains in liquid and/or supercritical fluid form. In certain embodiments, the electrochemical system and/or method is operated at a pressure such that the electrolyte remains in liquid form.

The electrochemical systems and/or methods described herein may be operated with an electrolyte at a variety of suitable ionic strength ranging from about 0 mM (e.g., water-based or organic solvent-based electrolyte) to up to about 10 M (e.g., a salt-based electrolyte such as a phosphate buffer), including, e.g., about 0 mM, about 0.5 mM, about 1 mM, about 5 mM, about 10 mM, about 25 mM, about 50 mM, about 100 mM, about 500 mM, about 1000 mM, about 5 M, or about 10 M. For example, in some embodiments, the electrochemical systems and/or methods described herein may be operated with an electrolyte at a suitable ionic strength for a target biomolecule to be separated such that the target biomolecule remains stable when it is bound to an electrode during application of an electrical potential.

The electrochemical systems and/or methods described herein may be operated at a variety of suitable pHs. In certain embodiments, the electrochemical system and/or method is operated with a neutral electrolyte (e.g., at about pH 7). In some embodiments, the electrochemical system and/or method is operated with an acidic electrolyte (e.g., below pH 7, e.g., about pH 6, about pH 5, about pH 4, or lower). In some embodiments, the electrochemical system and/or method is operated with a basic electrolyte (e.g., above pH 7, e.g., about pH 8, about pH 9, about pH 10, about pH 11, about pH 12, or higher).

In some embodiments of anion-selective separation, the electrochemical system and/or method is operated with an electrolyte at a pH above the isoelectric point of a target biomolecule to be separated. In some embodiments of cation-selective separation, the electrochemical system and/or method is operated with an electrolyte at a pH below that of the isoelectric point of a cation species to be separated.

In some embodiments, the electrochemical systems and/or method may be operated with an electrolyte at a suitable pH for a target biomolecule to be separated such that the target biomolecule remains stable when it is bound to an electrode during application of an electrical potential.

In some embodiments, the electrical potential applied to the electrodes (e.g., the first electrode and/or the second electrode) can be a positive potential or a negative potential depending on whether the electrode is an anode or a cathode. In some embodiments where the first or the second electrode is an anodic electrode, the anode electrode potential is equal to or less than about 2 V or lower, e.g., equal to or less than about 1.5 V, equal to or less than about 1.0V, equal to or less than about 0.8 V, equal to or less than about 0.6 V, equal to or less than about 0.4 V or lower. In some embodiments, the anode electrical potential can be at least about 0.1 V, at least about 0.2 V, at least about 0.3 V, at least about 0.4 V, at least about 0.5 V, at least about 0.6 V, at least about 0.7 V, at least about 0.8 V, at least about 0.9 V, or at least about 1.0 V. Combinations of the above-referenced ranges are also possible. For example, in some embodiments, the anode electrical potential may range from about 0.1 V to about 0.8 V. Other combinations are also possible. In some embodiments where the first or the second electrode is a cathodic electrode, the cathode electrode potential is equal to or less than 0 V or lower, e.g., equal to or less than about −0.1 V, equal to or less than about −0.2 V, equal to or less than about −0.3 V, equal to or less than about −0.4 V, equal to or less than about −0.5 V, equal to or less than about −0.6 V, equal to or less than about −0.7 V, equal to or less than about −0.8 V, equal to or less than about −0.9 V, or equal to or less than about −1.0 V, or lower. In some embodiments, the cathode electrical potential can be at least about −1.5 V or higher, including, e.g., at least about −1.4 V, at least about −1.3 V, at least about −1.2 V, at least about −1.1 V, at least about −1.0 V, at least about −0.9 V, at least about −0.8 V, at least about −0.7 V, at least about −0.6 V, at least about −0.5 V, at least about −0.4 V, at least about −0.3 V, at least about −0.2 V, or at least about −0.1 V. Combinations of the above-referenced ranges are also possible. For example, in some embodiments, the cathode electrical potential may range from about 0 V to about −1 V, or about 0 V to about −0.8 V, or about 0 V to about −0.5 V.

In some embodiments, the electrochemical systems and/or method may be operated with an electrolyte at a suitable electrical potential for a target biomolecule to be separated such that the target biomolecule remains stable when it is bound to an electrode during application of the electrical potential.

In some embodiments, the methods described herein involving electrosorption may be carried out at a current (e.g., constant current) of at least about 0.1 mA/cm$^2$, at least about 0.2 mA/cm$^2$, at least about 0.3 mA/cm$^2$, at least about 0.4 mA/cm$^2$, at least about 0.5 mA/cm$^2$, at least about 0.6 mA/cm$^2$, at least about 0.7 mA/cm$^2$, at least about 0.8 mA/cm$^2$, at least about 0.9 mA/cm$^2$, at least about 1.0 mA/cm$^2$, at least about 1.1 mA/cm$^2$, at least about 1.2 mA/cm$^2$, at least about 1.3 mA/cm$^2$, at least about 1.4 mA/cm$^2$, at least about 1.5 mA/cm$^2$, at least about 1.6 mA/cm$^2$, at least about 1.7 mA/cm$^2$, at least about 1.8 mA/cm$^2$, at least about 1.9 mA/cm$^2$, at least about 2.0 mA/cm$^2$, at least about 2.5 mA/cm$^2$, at least about 3.0 mA/cm$^2$, at least about 3.5 mA/cm$^2$, at least about 4.0 mA/cm$^2$, at least about 4.5 mA/cm$^2$, or at least about 5.0 mA/cm$^2$. In some embodiments, the methods described herein involving electrosorption may be carried out at a current (e.g., constant current) of no more than about 6.0 mA/cm$^2$, no more than about 5.0 mA/cm$^2$, no more than about 4.5 mA/cm$^2$, no more than about 4.0 mA/cm$^2$, no more than about 3.5 mA/cm$^2$, no more than about 3.0 mA/cm$^2$, no more than about 2.5 mA/cm$^2$, no more than about 2.0 mA/cm$^2$, no more than about 1.9 mA/cm$^2$, no more than about 1.8 mA/cm$^2$, no more than about 1.7 mA/cm$^2$, no more than about 1.6 mA/cm$^2$, no more than about 1.5 mA/cm$^2$, no more than about 1.4 mA/cm$^2$, no more than about 1.3 mA/cm$^2$, no more than about 1.2 mA/cm$^2$, no more than about 1.1 mA/cm$^2$, no more than about 1.0 mA/cm$^2$, no more than about 0.9 mA/cm$^2$, no more than about 0.8 mA/cm$^2$, no more than about 0.7 mA/cm$^2$, no more than about 0.6 mA/cm$^2$, no more than about 0.5 mA/cm$^2$, no more than about 0.4 mA/cm$^2$, no more than about 0.3 mA/cm$^2$, or no more than about 0.2 mA/cm$^2$. Combinations of the above-referenced ranges are also possible. For example, in some embodiments, the methods described herein involving electrosorption may be carried out at a current (e.g., constant current) of about 0.1 mA/cm$^2$ to about 2.0 mA/cm$^2$. In some embodiments, the methods described herein involving electrosorption may be carried out at a current (e.g., constant current) of about 0.5 mA/cm$^2$ to about 1.5 mA/cm$^2$. The current values provided herein refers to the magnitude of the current. The current can be positive or negative. The positive or negative references to the current refer to the direction of current flow depending on the electrical potential applied to the electrodes. In some embodiments, the methods described herein involving electrosorption may be carried out at a positive current (e.g., a constant positive current) of any of the above-referenced ranges. In some embodiments, the methods described herein involving electrosorption may be carried out at a negative current (e.g., a constant negative current) of any of the above-referenced ranges.

The methods described herein involving electrosorption may be carried out under an appropriate condition (e.g., appropriate pH, voltage, and/or current) until electrosorption of target biomolecules to an appropriate redox-electrode (e.g., the first electrode comprising a first redox-species as described herein) reaches equilibrium, which may vary with a number of factors including, e.g., but not limited to electrosorption kinetics, and/or kinetics of pseudocapacitive systems. Without wishing to be bound by theory, the relatively fast electron-transfer kinetics based on the surface Faradaic process can allow the methods described herein to be carried out in a short period of time, as compared to methods that rely on passive adsorption or non-electroactive conductive surfaces. For example, as shown in Example 1, for a potential swing of about 0.4V, about 60 seconds was more than sufficient for the current to reach equilibrium during charging and discharging. Thus, the methods and/or electrochemical systems described herein can be suitable for use as a platform for fast throughput bioseparation and/or analysis.

In some embodiments, the methods of various aspects described herein can be used to separate a first biomolecule from a second biomolecule in a solution, e.g., wherein the first biomolecule and the second biomolecule have different target functional groups or target functional sites, and/or various sizes, charge distribution, and/or isoelectric points. In some embodiments where the first redox-species of the first electrode is selective toward a certain target functional group or target functional site, the methods of various aspects described herein can be used to separate a biomolecule that does not have the target functional group, from a target functional group-comprising biomolecule. In some embodiments, the methods of various aspects described herein can be used to separate different biomolecules having the same or similar target functional groups or target functional sites based on, e.g., differences in sizes, charge distributions, dipole moments or internal dipole moments, and/or isoelectric points.

In some embodiments where different biomolecules sharing a common functional group or functional site, such biomolecules can be separated using the methods of various aspects described herein, for example, based on differences in sizes (e.g., a difference in molecular weight by at least about 25%, at least about 50%, at least about 100%, at least about 200%, at least about 300%, at least about 400%, at least about 500%, or higher). Accordingly, one aspect provided herein relates to a method for separating a first biomolecule from at least a second biomolecule in a solution, wherein the first biomolecule and the second biomolecule have different sizes (e.g., the first biomolecule has a smaller size than that of the second biomolecule). The method comprises: providing an electrochemical system or device comprising (i) a first electrode comprising a substrate (e.g., a solid substrate) and a first redox-species immobilized to the substrate (e.g., solid substrate), wherein the first redox-species is selective toward a target functional group or target functional site that is shared by the first biomolecule and the second biomolecule, based on a specific chemical interaction between the first redox species and the target functional group (or target functional site) of the first biomolecule and the second biomolecule, wherein the specific chemical interaction is activated by a Faradaic/redox reaction; and (ii) a second electrode, and wherein the first electrode and the second electrode are in contact with an electrolyte; (b) applying an electrical potential across the first electrode and the second electrode such that the first redox species of the first electrode transforms from a first redox state to a second redox state and selectively binds to the target functional group or the target functional site. In some embodiments, smaller biomolecules (e.g., a difference in molecular weight by at least about 25%, at least about 50%, at least about 100%, at least about 200%, at least about 300%, at least about 400%, at least about 500%, or higher) can bind to the first electrode in a greater amount (e.g., by at least about 25%, at least about 50%, at least about 100%, at least about 200%, at least about 300%, at least about 400%, at least about 500%) than other larger biomolecules, thereby separating biomolecules of different sizes.

In some embodiments where both the first and second biomolecules bind to the first electrode, the method may further comprise (c) reversing the electrical potential applied in step (b) across the first electrode and the second electrode such that either one of the first biomolecule and the second biomolecule is released from the first electrode while the other biomolecule remains bound to the first electrode. In these instances, the first biomolecule and the second biomolecule may adsorb to the first electrode to a similar or comparable extent during application of an electrical potential, but the first biomolecule and the second biomolecule may have different desorption behavior when the applied electrical potential is reversed (partially or completely including when the electrical potential is 0 V).

As another example, the methods of various aspects described herein can be used to separate a first biomolecule from a second biomolecule in a solution, wherein the first biomolecule and the second biomolecule differ in isoelectric points (e.g., a difference in isoelectric points by at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.5, at least about 3.0, at least about 3.5, at least about 4.0, at least about 4.5, at least about 5.0, at least about 6.0, at least about 7.0, at least about 8.0, at least about 9.0, at least about 10.0, at least about 11.0, at least about 12.0, or higher). Thus, the electrochemical devices described herein can be operated at a pH such that the first biomolecule and the second biomolecule have opposite charges, whereby the first biomolecule and the second biomolecule are captured on different electrodes.

In other embodiments, the methods of various aspects described herein can be used to separate a first biomolecule from a second biomolecule in a solution, wherein the first biomolecule and the second biomolecule differ in dipole moments (e.g., a difference in dipole moments by at least about 20%, at least about 25%, at least about 30%, at least about 40%, at least about 50%, at least about 100%, at least about 200%, at least about 300%, at least about 400%, at least about 500%, or higher). A higher dipole moment value is generally indicative of a more polar biomolecule. As shown in Example 1, the redox-interfaces of the electrodes exhibited a preferential affinity for biomolecules having higher dipole moments.

In some embodiments where the electrochemical systems described herein is operated under a condition at which an enzyme remains stable when it is reversibly attached to an electrode during application of an electrical potential, such electrochemical systems with an enzyme reversibly attached to an electrode can be used for biosensing and/or biocatalysis. Accordingly, another aspect described herein relates to a method of preparing an electrochemical system for biocatalysis or biosensing. The method comprises: (a) contacting an aqueous solution comprising an enzyme with (i) a first electrode comprising a substrate (e.g., a solid substrate) and a first redox-species immobilized to the substrate (e.g., solid substrate), wherein the first redox-species is selective toward a target functional group or target functional site of the enzyme based on a specific chemical interaction between the first redox species and the target functional group or target functional site, wherein the specific chemical interaction is activated by a Faradaic/redox reaction; and (ii) a second electrode; and (b) applying an electrical potential across the first electrode and the second electrode to activate the Faradaic/redox reaction such that the first redox species transforms from a first redox state to a second redox state and selectively binds to the target functional group of the enzyme, wherein the enzyme remains stable during application of the electrical potential, thereby preparing an electrochemical system comprising the enzyme reversibly attached to the first electrode.

In some embodiments, the first electrode is an anodic electrode. In these embodiments, the enzyme may be a neutrally-charged enzyme (e.g., an enzyme with a net charge of zero) comprising at least one negatively-charged domain, or a negatively-charged enzyme (e.g., an enzyme with a negative net charge).

In some embodiments, the first electrode is a cathodic electrode. In these embodiments, the enzyme may be a neutrally-charged enzyme (e.g., an enzyme with a net charge of zero) comprising at least one positively-charged domain, or a positively-charged enzyme (e.g., an enzyme with a positive net charge).

As used herein, the term "stable" refers to an enzyme retaining at least about 50% or more (including, e.g., at least about 60%, at least about 70%, at least about 80%, at least about 90%, at least about 95%, at least about 98%, at least about 99%, and up to 100%) of its biological or enzymatic activity. In some embodiments, an enzyme remains stable when it is bound, adsorbed, or attached onto an electrode during application of an electrical potential. In some embodiments, the enzyme may retain at least about 50% or more (including, e.g., at least about 60%, at least about 70%, at least about 80%, at least about 90%, at least about 95%, at least about 98%, at least about 99%, and up to 100%) of its biological or enzymatic activity, upon its release from the electrode. In some embodiments, an enzyme may remain stable after at least 2 adsorption-desorption cycles, including, e.g., at least 3, at least 4, at least 5, at least 10, at least 20, at least 30, at least 40, at least 50, at least 100 or more adsorption-desorption cycles.

As used herein, the term "reversibly" refers to the binding, adsorption, or attachment of an enzyme onto an electrode surface being reversible by modulation of an electrical potential applied across electrodes. For example, an enzyme can bind, adsorb, or attach onto an electrode surface upon application of an electrical potential, and can then be released from the electrode surface by reversing the electrical potential.

A variety of enzymes classes can be used to prepare such an electrochemical system for biocatalysis or biosensing, including, for example, but are not limited to oxidoreductases (e.g., oxidases such as glucose oxidase, oxygenases, peroxidase, dehydrogenases, laccases, lypoxygenases), transferases (e.g., glycosyltransferases, fructosyltransferases, transglutaminases, transketolases, methyltransferases, transaldolases, acyltransferases, transaminases), hydrolases (e.g. esterases, lipases, proteases, glycosidases, phosphatases, amylases, glucanases, invertases, petidases, phytases, xylanases, phospholipases), lyases (e.g., decarboxylases such as aceolactate decarboxylases), aldolases, ketolases, hydratases, dehydratases, isomerases (e.g., racemases, epimerases, isomerases such as xylose isomerase), ligases (e.g., synthetases, carboxylases), muramidase or N-acetylmuramide glycanhydrolase (e.g., lysozymes), proteases (e.g., trypsin, chymotrypsin, endoproteinas, aminopeptidase) or antimicrobial enzymes (e.g., lysozymes). Additional examples of enzymes that can be used to prepare such an electrochemical system for biocatalysis or biosensing include, but are not limited to glucose isomerase, nitrile hydratase, lactase, penicillin G acylase, and/or thermolysin.

Accordingly, various biocatalytic systems produced by such a method are also provided herein. Appropriate enzyme can be selected to prepare a biocatalytic system for a particular reaction. For example, horseradish peroxidase (HRP) is a heme-containing enzyme that can catalyze oxidation of a wide variety of organic and inorganic compounds. HRP C can be used for enantioselective oxidations as an alternative to organometallic catalysts. Accordingly, HRP C can be reversibly attached to an electrode of an electrochemical system using one embodiment of the methods described herein. For example, upon electrical stimulation, HRP C can be reversibly attached to an oxidized state of an electrode comprising a metallocene, e.g., ferrocene, forming a biocatalytic system which can be used to perform enantioselective oxidation in the presence of HRP C as a biocatalyst.

In a further aspect, the present disclosure provides a method comprising performing biocatalysis in the biocatalytic system described herein, wherein an electrical potential is applied across the first electrode and the second electrode to activate the Faradaic/redox reaction such that the enzyme is reversibly attached to the first electrode and remains stable during application of the electrical potential. In some embodiments, the method can be used to provide an electrochemically-controlled biocatalyst support for heterogeneous catalysis.

Various embodiments of the methods of various aspects described herein can further comprise reversing the applied electrical potential (e.g., partially or completely reversal including when the applied electrical potential is off, i.e., V=0) to release the bound target biomolecule and/or captured cationic species from the electrodes. In some embodiments, the methods of various aspects can be used to provide an electrochemically-reversible adsorbent material. Such an electrochemically-reversible adsorbent material can be used in various applications, including, e.g., but not limited to bioseparations, protein purifications, biocatalysis, and electrochemically mediated drug releases.

The electrode systems described herein can be cycled for at least 200 cycles or more with a minimal loss (e.g., less than 10% loss, or less than 5% loss) in electrochemical charge. In some embodiments, the electrode systems can be cycled for at least 300 cycles, at least 400 cycles, at least 500 cycles, at least 600 cycles, at least 700 cycles, at least 800 cycles, at least 900 cycles, at least 1000 cycles, or more, with a minimal loss (e.g., less than 10% loss, or less than 5% loss) in electrochemical charge.

In some embodiments where the first and second electrodes are asymmetric redox-activated (e.g., first and second electrodes have redox species of different charges and chemical identity), the electrochemical devices or systems have the capability of suppressing parasitic reactions that would be otherwise present in electrochemical systems without asymmetric redox-activated electrodes, thus increasing separation as well as energy storage performance. This is applicable for both organic solvent phase-based and water phase-based application (e.g. suppression of electrolyte destruction, prevention of water reduction or water oxidation).

Other features or advantages of the present disclosure will be apparent from the following drawings and Examples, and also from the appended claims.

EXAMPLES

Example 1: Nanostructured Redox-Interfaces for Electrochemically-Controlled Interaction with Proteins: Bio-Separations and Heterogeneous Enzyme Catalysis Proteins are amphiphilic biomacromolecules of great importance for biotechnology, therapeutics, and genetic engineering. The interaction of proteins with advanced material interfaces has been reported in the context of self-assembly, bio-adsorption and permeation, with nanostructures ranging from organic and inorganic to composites. More recently, protein interactions with organic conducting polymers and under electrical stimuli have received increased attention for applications as varied as tissue engineering to sensing and bio-separations. Stimuli-responsive interfaces represent a key direction in development of nanostructured and robust materials for biological applications. In this Example, chemically-functionalized, nanoporous redox-active electrodes were developed as a platform to modulate the surface affinity of proteins and enable reversible electrosorption and release, for the purposes of bio-separations. In addition, the performance of these interfaces were demonstrated herein as highly efficient, non-destructive catalyst immobilization.

Studies of protein interaction with charged-interfaces, both from an applied and fundamental perspective, are of importance in the design of more efficient electrochemically-mediated systems for biological applications. However, for electrochemical-type systems, previous designs have been mostly limited to conducting electrodes that are not electro-active. Faradaic processes at the electrode interface offer advantages that include faster electron-transfer, reversibility, and through modulation of potential, the possibility for achieving molecular selectivity at relatively low overpotentials. Heterogeneous redox-species have been used, among others, for electrocatalysis, analyte recognition, and pseudocapacitive charge storage. Recently, ferrocene-functionalized electrodes have been shown to selectively bind organic anions over competing anions based on specific chemical interactions. Ferrocene, when oxidized to ferrocenium, has shown the ability to reversibly bind carboxylates over competing anions in over 33-fold excess through redox-activated hydrogen bonding of the organic functional groups with the cyclopentadienyl, thus providing remarkable molecular selectivity. In turn, proteins have a predominance of carboxylic acids in their amino-acid building blocks, and at the molecular level it is this charge distribution that dictates many of the physic-chemical properties of these bio-macromolecules.

Protein separation has been a primary challenge of biotechnology for the past decades, and with the advances of both functional materials as well as increasing demands in selectivity, there is a need to develop novel materials and methods for protein separation. Electrochemically-based separations can have significant advantages over traditional ion-exchange methods, as they have dramatically faster kinetics for adsorption of charged species, re-usability by reversible adsorption and most importantly, do not need chemical regenerants or changes in pH which often account for much of the chemical costs of separation. All these advantages also lead to modularity and ease of scale-up. Conventional methods however are limited by their ion-capacity, which is often very low (in the 10 mg/g range at most) and most importantly, when utilized for bio-separations, it can affect the integrity of the proteins based on the degree of overpotential utilized. In this Example, it was sought to explore whether redox-active interfaces can modulate binding with these bio-macromolecules and also to identify practical application of redox-active materials. It is presented herein that the redox-based materials described herein provide a solution to circumvent both challenges— through the high pseudocapacitance and charge storage, and the ion-capacity of the systems described herein can be increased beyond that of capacitive-type electrosorption. In addition, the overpotentials can be maintained at the low to moderate redox-potentials of active species. Furthermore, selectivity of redox-surface affinity towards a native protein can be advantageous over specific affinity tags, for example, by eliminating the need to perform post-translational modifications.

The preservation of proteins at the interface of the functionalized surface of the systems described herein without degrading their structure represents a significant step for enzymatic catalysis. Heterogeneous enzyme catalysis is an important field of research for bioprocessing and the chemical industry, due to the potential reuse and recovery of the catalysts. Application in fixed-bed reactor configurations and optimal performance in non-aqueous media; with a variety of porous materials have been discussed as potential attachment substrates. Various covalent methods for enzymatic immobilization affect the chemical structure and decrease the activity, whereas porous confinement is often susceptible to leaching. Electrostatic combined with surface affinity, however, can provide a strong immobilization without actually forming any damaging chemical bonds. By maintaining the supporting surface at a moderate potential, high enough to oxidize the redox-binding sites but low enough to prevent peptide degradation, a heterogeneous surface that has minimal effect on enzyme activity is achieved. In addition, due to the reversibility of the electrode surface by modulation of electrical potential, the electrode surface can provide multiple enzymatic sites for cascade reactions or boomerang catalysis.

In this Example, how nanostructured ferrocene-functionalized redox-electrodes can be used for modulating the interfacial interaction with proteins was investigated, and redox-based systems for both reversible, potential-modulated electrosorption as well as immobilized enzyme catalysis were assessed. It is shown that non-covalent chemical interactions preserve bio-activity both in the supported and released form. A range of proteins ranging from the tens to hundreds of kilodalton was explored, and a series of enzymes was also explored for measuring their catalytic activity. In addition to the aforementioned applications, the system can be used as a platform for sensing and even potential-controlled therapeutic release.

Results and Discussion

Redox-electrodes.

Figure 1B:
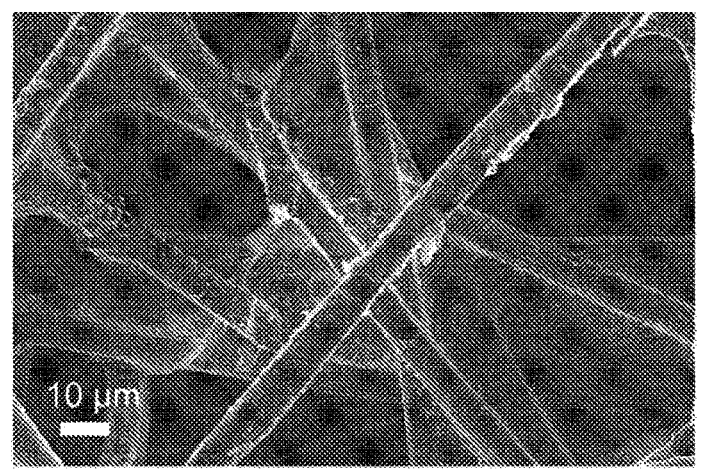
FIGS. 1B-1C show HR-SEM of dip-coated PVF/CNT electrode surface on carbon fibers at various magnifications.
Figure 1C:
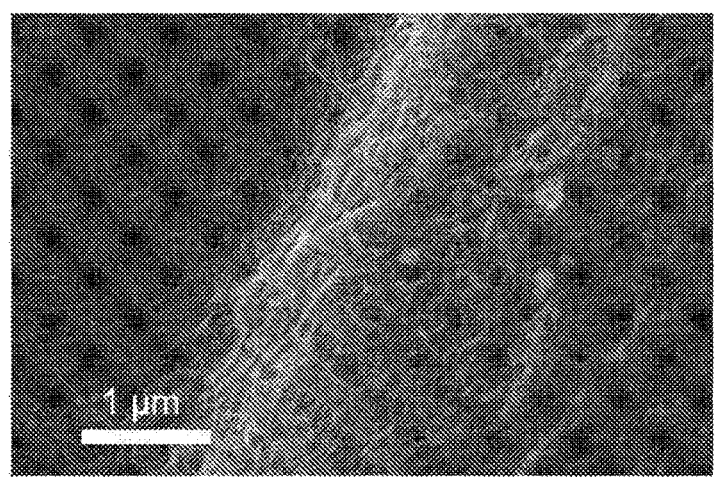
Figure 1D:
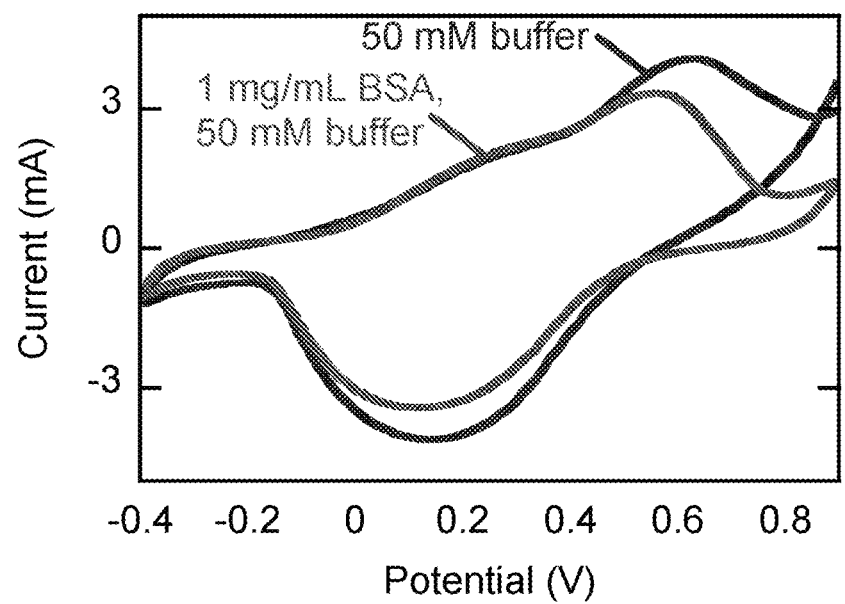
FIG. 1D shows the cathodic shift in oxidation peak from cyclic voltammetry at 0.05 V/s of PVF-CNT in 50 mM phosphate buffer with and without BSA.
Figure 7:
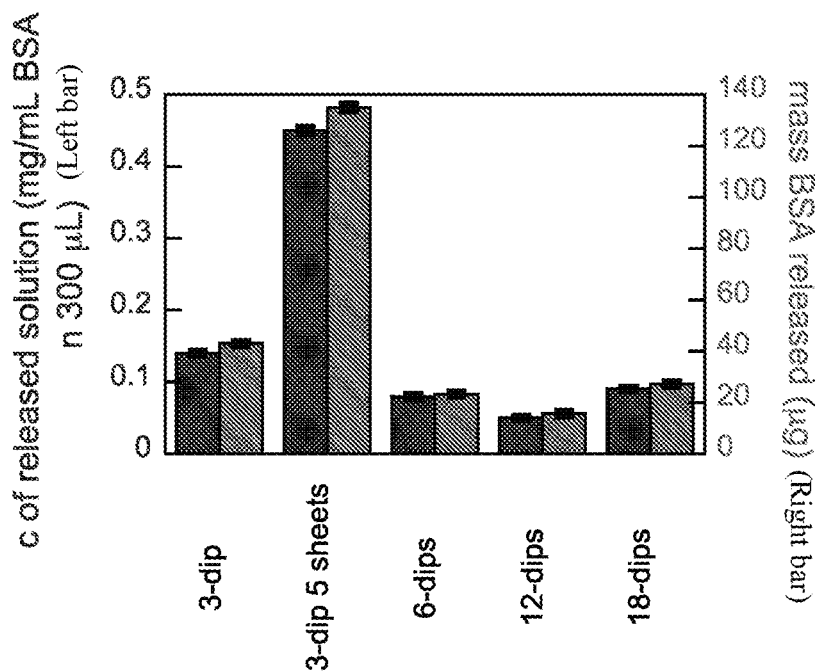
FIG. 7 is a graph showing the surface area dependence of adsorption based on dip-control.

The redox electrodes were prepared by dip-coating conductive carbon fibers (Electrochem Inc.) in a 1:1 solution of poly(vinyl)ferrocene (PVF) and carbon nanotubes (CNT); the carbon fibers provide a stable support for the functional material (FIG. 1A—details given in the experimental and computational methods). The PVF/CNT coating forms a porous conductive layer around the carbon fibers (FIGS. 1B and 1C) with pores at a nano-scale. Cyclic voltammetry at 10 mV/s showed a linear dependence of charge on the number of dip-layers coating the electrode. In one example, 3-layer coating was found to be optimal for both film morphology as well as maximizing protein adsorption per adsorbent mass; any additional layers do not increase uptake due to accessibility of the inner redox sites to the protein (see FIG. 7). In the presence of proteins (e.g. at 1 mg/mL BSA and 50 mM phosphate buffer at pH=7), there was a cathodic shift in the formal potential of ferrocene, indicating a favorable binding interaction between the redox-species and the proteins in solution (FIG. 1D). However, as compared to small-molecule sensing, broader voltammograms were observed in the case of proteins due to the heterogeneous nature of the interactions and greater mass transfer limitations.

Bovine serum albumin (BSA) and alpha-chymotrypsin ($\alpha$-CHY) were chosen as the model proteins for proof-of-concept. In the first set of electrosorption tests, adsorption of BSA was performed at pH=7, 50 mM phosphate buffer, and of $\alpha$-CHY at pH=11, 50 mM carbonate, to make sure that all proteins were significantly negatively charged (zeta potential of −25.55 mV for BSA and −32.44 mV for $\alpha$-CHY). To reach equilibrium uptake capacities, the electrosorption was carried out at a constant current of +100 µA (~1 mA/cm$^2$ current density) to the poly(vinyl)ferrocene (PVF)/carbon nanotube (CNT) electrode for 10 min. Phosphate buffer at 50 mM was used as the supporting electrolyte, with a 1 mg/mL concentration of protein from the adsorption stock solution. To recover the proteins, the loaded PVF/CNT electrode was immersed in a clean buffer solution at the same pH and ionic strength as used for adsorption, and a current of −100 µA was applied to drive the reduction of the ferrocenes and release the adsorbed proteins. In between the adsorption and desorption, the platinum counter-electrode was switched and cleaned extensively to discriminate only the effect of the PVF-CNT electrode. The electrical potential of the system stabilized at between 0.3 V and 0.4 V during oxidation, which corresponded to the peak oxidation of the ferrocene-ferrocenium couple, and reflected the pseudocapacitive nature of the system. Similar protein uptake was observed with chronoamperometry (+0.4 V) as with chronopotentiometry, but less than 60 seconds were needed to charge the electrodes, demonstrating the remarkable kinetics of these pseudocapacitive systems.

Protein Electrosorption.

Figure 2A:
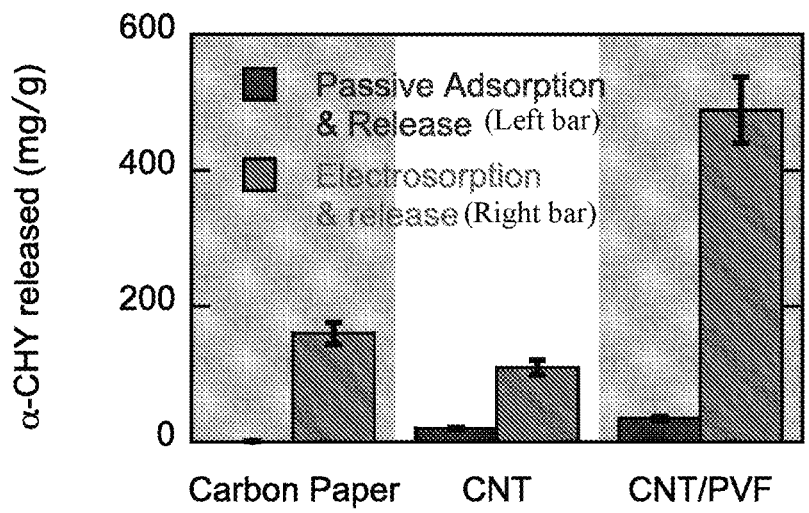
FIG. 2A is a graph showing α-chymotrypsin (α-CHY) uptake (mg proteins/g adsorbent) at pH=11 (50 mM carbonate), desorption at pH=7.
Figure 2B:
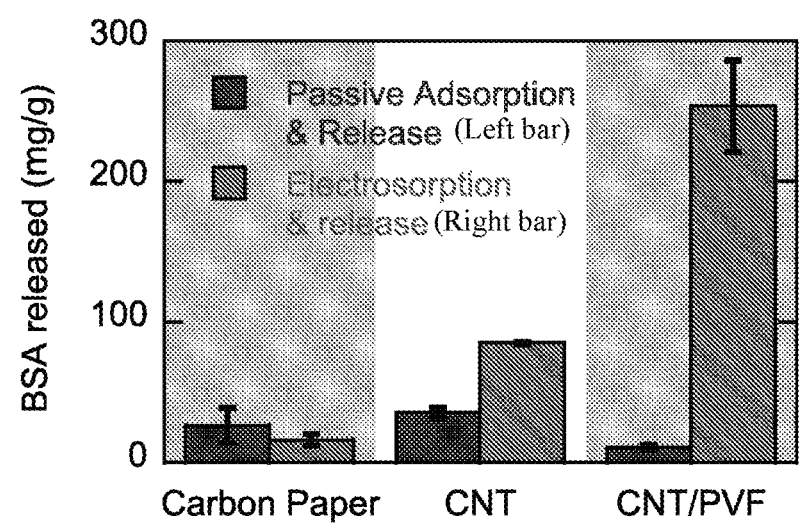
FIG. 2B is a graph showing bovine serum albumin (BSA) adsorbed at pH=7 (50 mM phosphate) and desorbed at pH=7 (50 mM phosphate).
Figure 8:
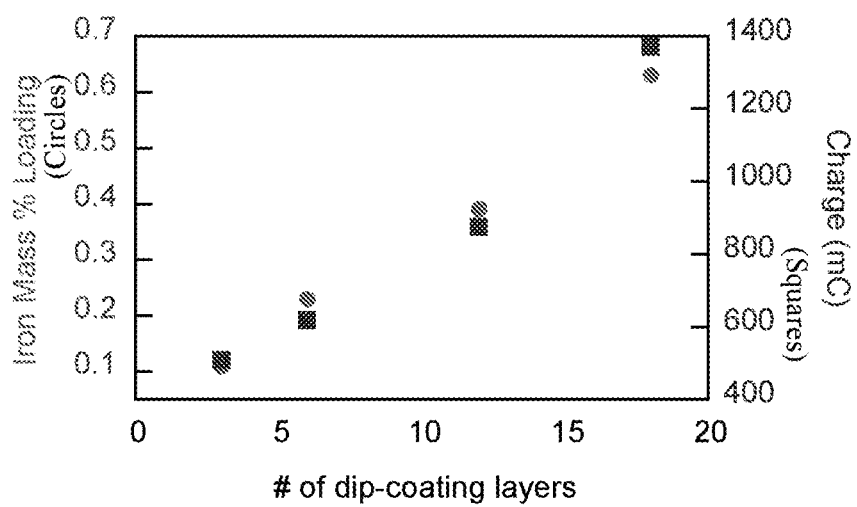
FIG. 8 shows the relationship of iron loading (% mass from ICP) with electrochemical capacitance obtained from CV at 0.05 V/s, 100 mM $LiClO_4$.

The uptake of proteins on the redox-electrodes was quantified via a bicinchoninic acid (BCA) assay on the supernatant. Bare conductive carbon fibers (CF) and fibers coated solely with carbon nanotubes (CNT) were used as controls. Negligible passive adsorption was observed when the various electrodes were soaked in the protein solutions for up to 8 hours. There was some limited protein uptake with positively polarized CNT electrodes, which was probably due to the electrical double-layer (FIG. 2A). On the other hand, oxidized PVF/CNT adsorbed almost three-fold more $\alpha$-CHY than did the conductive CNT electrode (43 µg/electrode with CNT/PVF vs 14.4 µg/electrode with CNT), with similar results seen for BSA (FIG. 2B). In sum, in terms of protein uptake, the redox-electrodes showed much higher protein capacities than did the non-electroactive conductive surfaces. Elemental analysis by inductively coupled plasma (ICP) indicated that each 3-layer electrode contained an average of 0.11% weight iron (FIG. 8), which when converted results in 84.8 µg of PVF and 169.6 µg total adsorbent mass per electrode (PVF+CNT). As such, specific uptake capacities herein are based on protein successfully released after sorption divided by this average adsorbent mass, which in the case of $\alpha$-CHY, corresponds to ~200 mg/g. The redox electrode mass-based specific uptake values are comparable and often superior to various high-capacity porous adsorbents in literature, ranging from silica beads, porous polymers to magnetic particles. Also, based on specific area, the adsorption of $\alpha$-CHY and BSA at pH=7 were 18.7 µg/cm$^2$ for $\alpha$-CHY and 13.4 µg/cm$^2$ for BSA (based on geometric surface area) are significant higher equilibrium values than those observed with various conventional polymeric and inorganic materials. In addition to the high capacities, the interaction of the proteins with the redox-electrodes was shown to be successfully tunable by electrochemical potential, e.g., mediated by the redox-reversibility of the ferrocene units.

Figure 2C:
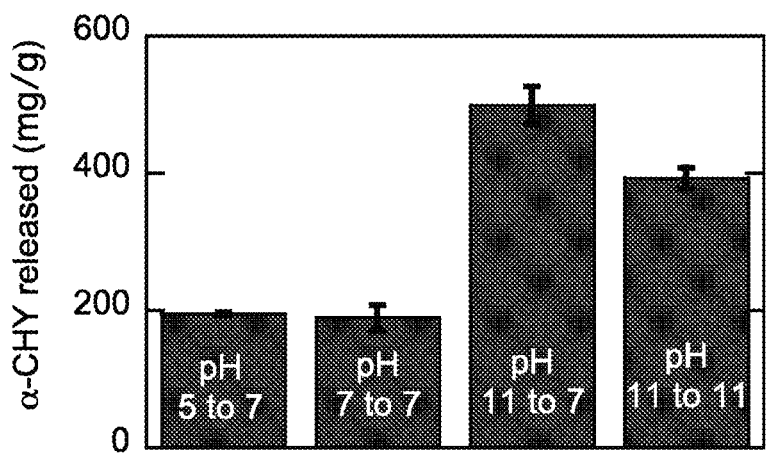
FIG. 2C is a graph showing the effect of solution pH on α-CHY adsorption.

There was a significant effect of pH on the protein charge distribution, which in turn affected adsorption performance. There was lower adsorption at lower solution pH owing to the more positive surface charge (FIG. 2C). On the other hand, the pH of the release buffer did not play a major role in desorption (whether at pH=7 or 11), as ~80% of the protein was able to be desorbed at the same pH as that at which the adsorption step was carried out. Moreover, the adsorption capacity was found not to be affected significantly by the ionic strength of the phosphate solution (0 mM, 25 mM, 50 mM, and 100 mM), which was a surprising finding as polymeric charged and zwitterionic systems suffer from lower capacity at low ionic strengths. Without wishing to be bound by theory, this independence of adsorption capacity with respect to ionic strength can be attributed to the ion-selectivity nature of the receptor ferrocene units, which are shown to present a 1:1 stoichiometry towards carboxylates, and thus are primarily selective towards the anionic groups on the proteins over any competing electrolyte tested, be it phosphate or perchlorate.

Multiple Proteins.

Figure 2D:
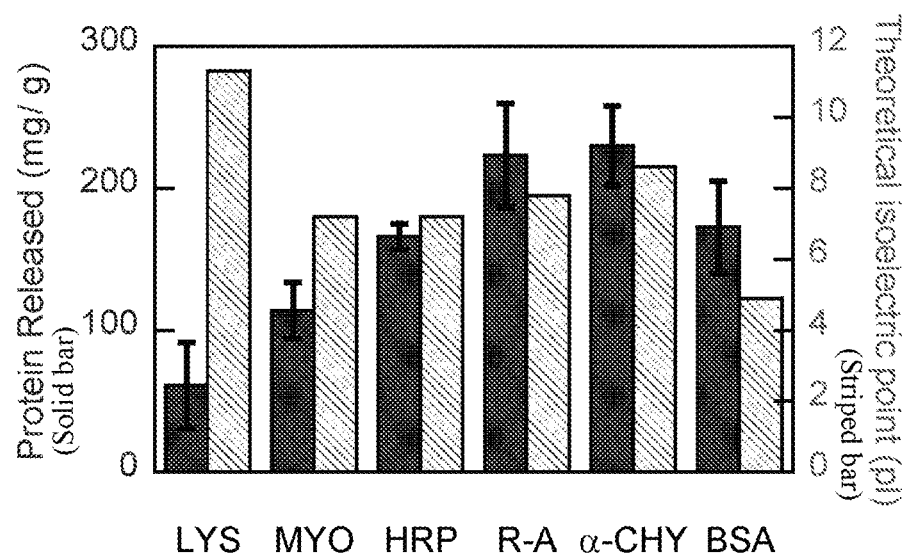
FIG. 2D is a graph showing the adsorption capacity of the PVF-CNT redox-electrode towards various proteins at pH=7 (LYS: lysozyme, MYO: myoglobin, HRP: horse-radish peroxidase).
Figure 2E:
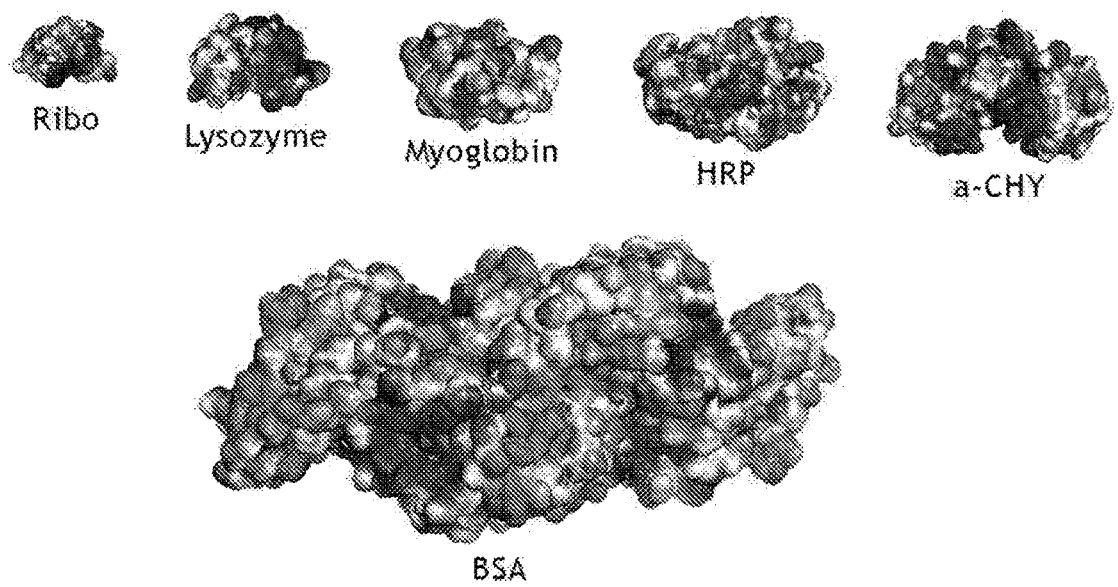
FIG. 2E shows charge electrostatic mapping in various proteins at pH=7 by accounting for protons, 50 mM ionic strength calculated based on an adaptive Poisson-Boltzmann solver.

A range of proteins with various isoelectric points, sizes and charge distribution were tested to investigate the generality of the system described herein, ranging from small proteins from 14 kDa to large 60 kDa, and a pI range from 4 to 11 (Table 1). As shown in FIG. 2D, under chronopotentiometry, the redox-interaction with the proteins was only seen to be dependent on isoelectric point in the more extreme cases, such as lysozyme (pI~11), which is significantly positively charged and thus has very low uptake (<80 mg/g) when compared to other small proteins, such as ribonuclease (pI~7, uptake >200 mg/g). For proteins with similar isoelectric points, possible differences in uptake can be due to effects such as hydrophobic or hydrophilic effects, as well as particle size and the charge distribution. The relatively higher uptake capacity of smaller proteins such as myoglobin and ribonuclease (size ~14-17 kDa) when compared to BSA (~60 kDa), which has a much lower pI, could be due to their more concentrated charge and better geometrical stacking on the surface of the porous electrodes. The spatial distribution of the protein charges was plotted by using a Poisson-Boltzmann solver (APBS & PDB2PQR) which accounts for all side-chain pKa's using PROPKA and accounting for ionic strength of 50 mM, and were plotted at scale (FIG. 2E), with negative charges in red and positive charges in blue. For example, the relatively high adsorption of ribonuclease and α-CHY could be due in part to their internal polarizability, with their anionic and cationic domains being more segregated within the particle (FIG. 2E) and thus providing pockets of interaction with the uniformly distributed oxidized redox-species on the surface.

The internal dipole moments for each protein were estimated (Table 1) by using the Weizmann Institute of Science's dipole moment server based on each protein's PDB file, e.g., as described in Felder et al. Nucleic Acids Research 2007, 35, W512. As shown in Table 1 and FIG. 2E, chymotrypsin and ribonuclease, which have more polarized charged groups (positive and negative) and higher dipole moments (819 and 659 Debye) than other tested proteins, exhibited higher uptake, indicating a preferential affinity of the redox-interfaces for more polarized proteins. The region of protein which is contact with the surface material does need to bear the same sign as the entire protein itself, and is dictated by the local electrostatic environment, which may explain why isoelectric points (reflecting overall protein charge) do not seem to play a huge role as in local heterogeneities. Surface charges and charge distribution, based on the so-called charge regulation mechanism (see, e.g., Hartvig et al. Langmuir: the ACS journal of surfaces and colloids 2011, 27, 2634; and Biesheuvel et al. Journal of Physical Chemistry B 2005, 109, 4172), can play a crucial role at determining preferential affinity of proteins of similar size with an interface, especially one that is chemically selective and redox-functionalized.

TABLE 1

Size and charge properties of tested proteins. Values were obtained from common literature sources. The isoelectric points are subject to significant deviations depending on buffer conditions. The dipole moments were calculated from the Protein Dipole Moments Server (PDMS) based on each protein's PDB file, taking only the peptide sequence. See, e.g., Janson, J.-C. Protein Purification: Principles, High Resolution Methods, and Applications; John Wiley & Sons, Inc.: Hokoben, New Jersey, 2011; Adler-Abramovich et al. ACS Nano 2016, 10, 7436; and Felder et al. Nucleic Acids Research 2007, 35, W512, for information on determination of size and charge properties of tested proteins.

| Protein Name | Approximate size (Da) | Isoelectric point (PI) | Internal Dipole Moment (Debye) |
|---|---|---|---|
| Lysozyme (LYS) | 14,000 | 11.3 | 216 |
| Myoglobin (MYO) | 16,900 | 7.2 | 239 |
| Horse-radish peroxidase (HRP) | 44,000 | 7.2 | 188 |
| Ribonuclease-A (R-A) | 14,700 | 7.8 | 819 |
| α-chymotrypsin (α-CHY) | 25,000 | 8.6 | 659 |
| Bovine serum albumin (BSA) | 66,500 | 4.9 | 579 |

Figure 3A:
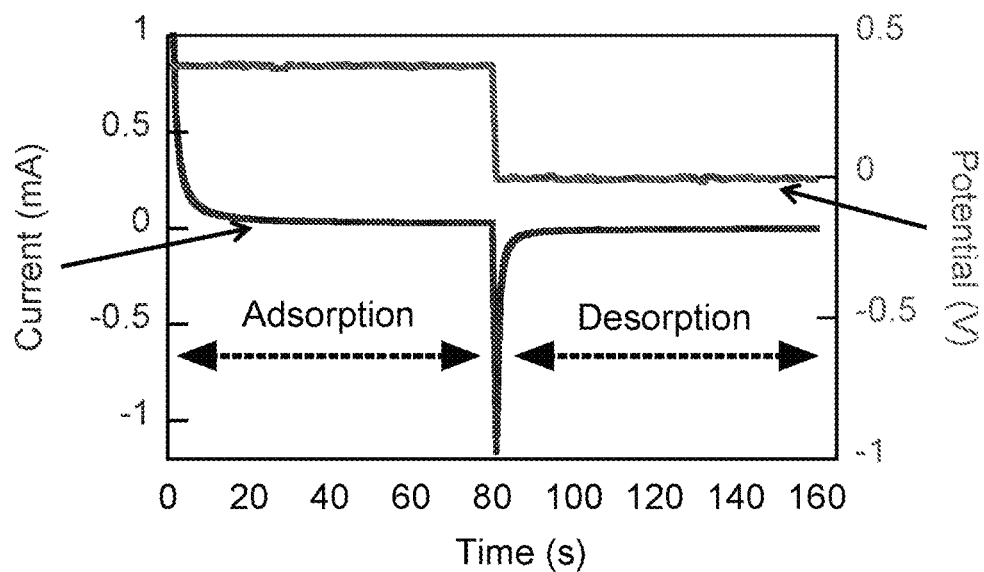
FIGS. 3A-3B show selective separation in a binary protein mixture (MYO/BSA, 1 mg/mL each in pH=7 50 mM)
Figure 3B:
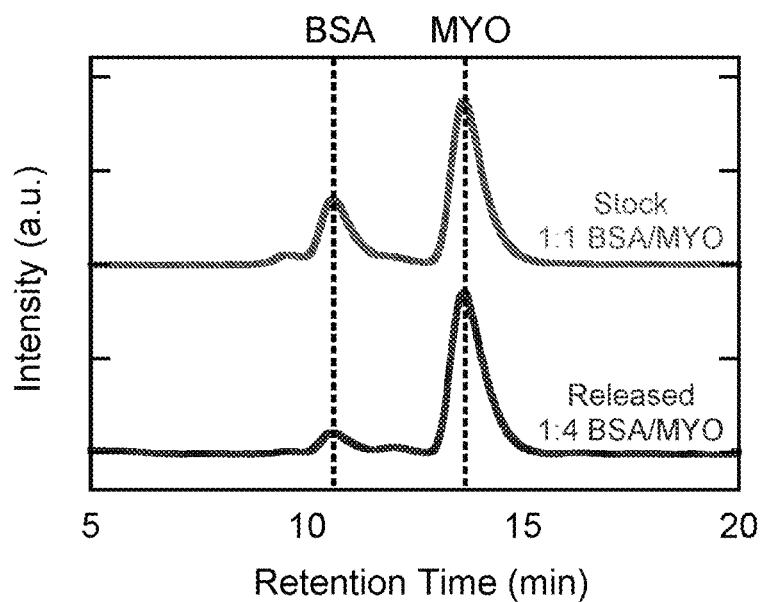
Figure 12:
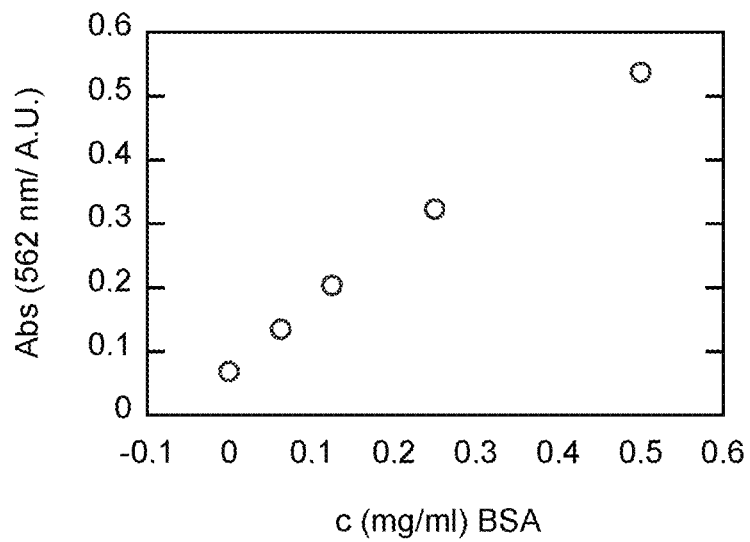
FIG. 12 shows the BSA calibration standard which serves as substitute for the micro-BCA calibration.

The selectivity of the redox-electrode between different proteins was investigated by electrosorption and release from a binary mixture (+0.4 V adsorption, and 0 V desorption) in 50 mM phosphate (1 mg/mL BSA+1 mg/mL MYO, pH=7 in water 50 mM phosphate buffer). As shown in FIG. 3A, for a potential swing of 0.4 V, 60 seconds was more than sufficient for the current to reach equilibrium during both charging and discharging, thus highlighting the relative electron-transfer fast kinetics of the system based on the surface Faradaic process, and indicating that these type of pseudocapacitive systems can be used as a platform for fast-throughput separations and analysis. When compared to standard chromatography techniques, electrochemical systems have the potential to be significantly faster, in addition to being more chemical selective, based on electrostatic migration effects in addition to concentration diffusion. From the single-electrode adsorption, BSA and MYO were shown to have similar uptakes—yet these proteins are of significantly different properties (Table 1). BSA is a much larger protein than MYO, making a binary mixture separation between the two species of different sizes an interesting case to investigate. Using a size-exclusion column in a fast protein liquid-chromatography (FPLC), it is found that that significantly more myoglobin (MYO) is desorbed than BSA (FIG. 3B), denoting that in the case of proteins of different size, the electrode is preferential towards the smaller ones even beyond pI effects. By integrating the peaks and compared with appropriate standards (FIG. 12) a separation factor of 3.9 can be achieved between myoglobin and BSA based on an equimolar adsorption mixture.

Electrode Re-Usability and Protein Binding Stability.

Figure 4A:
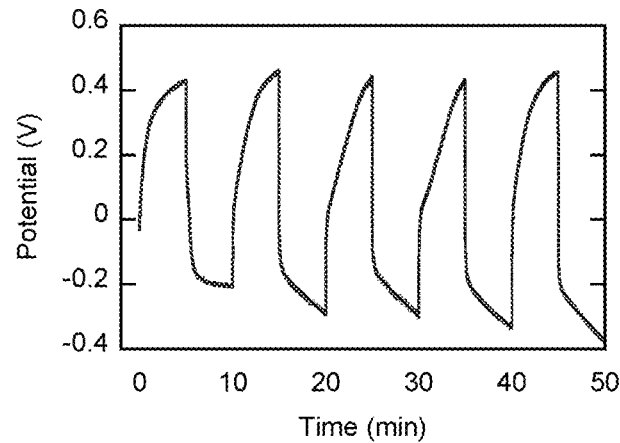
FIG. 4A shows the α-chymotrypsin (α-CHY) current-voltage response during cycling adsorption in pH=7.
Figure 4B:
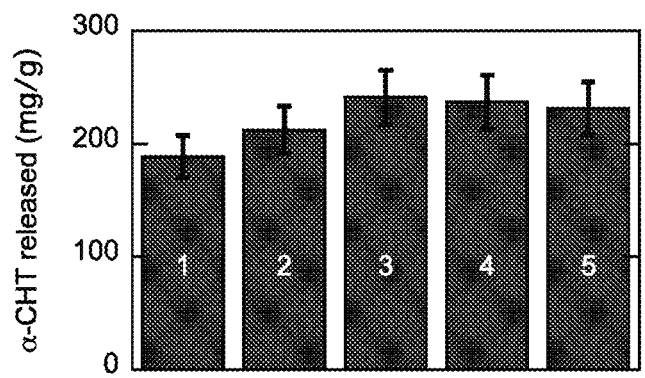
FIG. 4B shows the mass of protein released during each subsequent cycle.
Figure 4C:
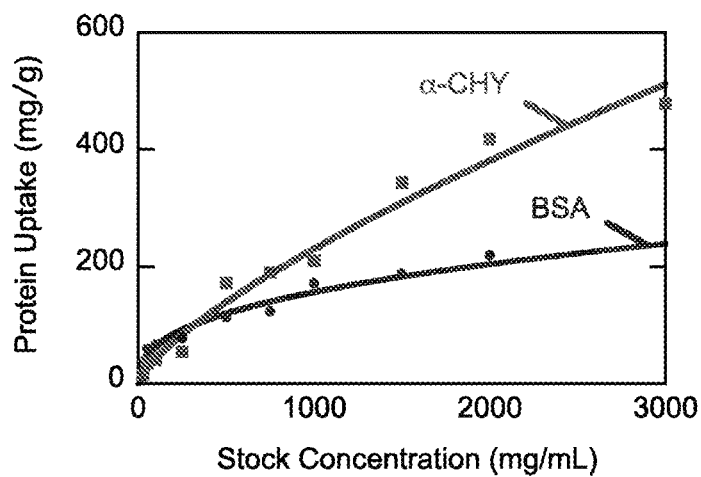
FIG. 4C shows α-CHY and BSA adsorption isotherms for electrochemical adsorption at pH=7, 50 mM phosphate buffer.

Furthermore, the electrode was stable after 5 consecutive adsorption and desorption cycles (FIGS. 4A and 4B) and maintained a constant adsorption capacity (~200 mg/g), showing both electrochemical stability as well as regenerability for bioseparations. From adsorption isotherms (FIG. 4C) obtained by chronopotentiometry of PVF/CNT at various protein concentrations (+100 µA, equilibrium potential ~0.4 V), α-CHY showed a significant higher adsorption capacity at low to moderate concentrations than did BSA, with both displaying significant uptake across a range of concentrations down to 100 µg/mL. These isotherms agree with the adsorption behavior on porous interfaces, where the relative protein amounts adsorbed increase proportionally with protein solution, and the adsorption amounts of various proteins at different concentrations vary with a series of factors including, e.g., molecular packing, size, charge, chemical affinity, and hydrophobicity.

Figure 5A:
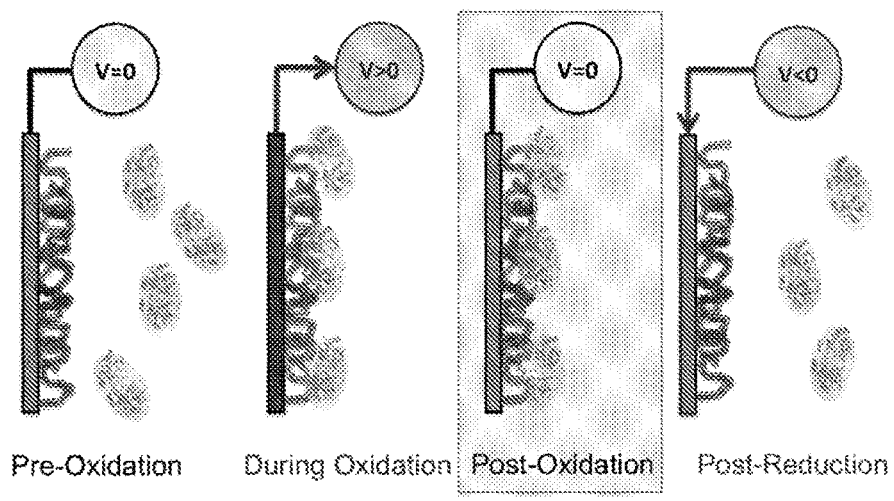
FIG. 5A shows a schematic of the various steps in which electrosorption can occur during the adsorption and desorption of α-CHY by potential.
Figure 5B:
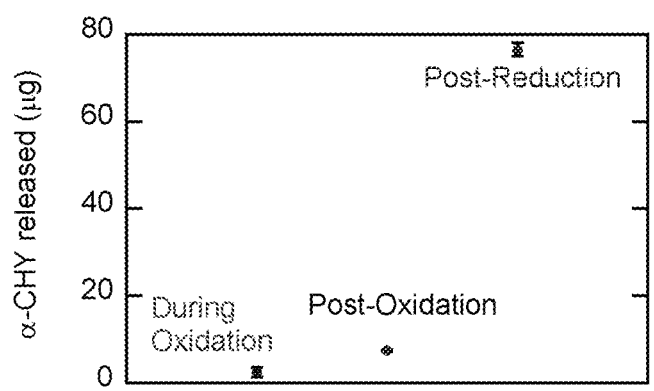
FIG. 5B shows the α-CHY released during Step 1) oxidation by assaying clean buffer solution with electrode constantly under potential, Step 2) post-oxidation of enzyme before reducing the electrode, and Step 3) after full release of protein by applying reducing current or voltage in pH=7 to pH=7.
Figure 5C:
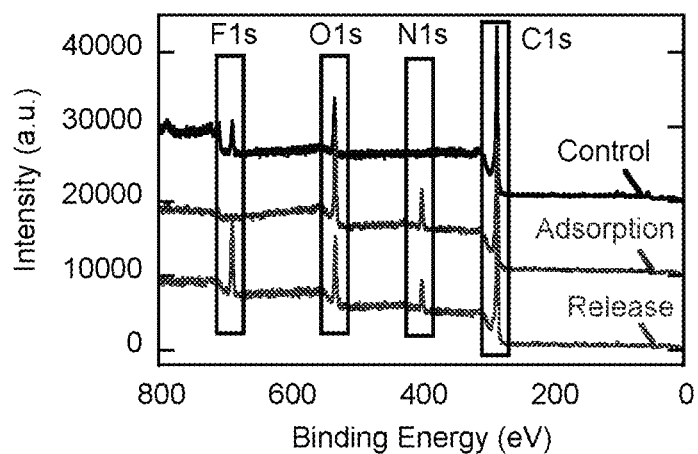
FIG. 5C shows XPS on surface PVF-CNT electrode to track protein on the surface of the electrode before, after adsorption and after release.
Figure 9:
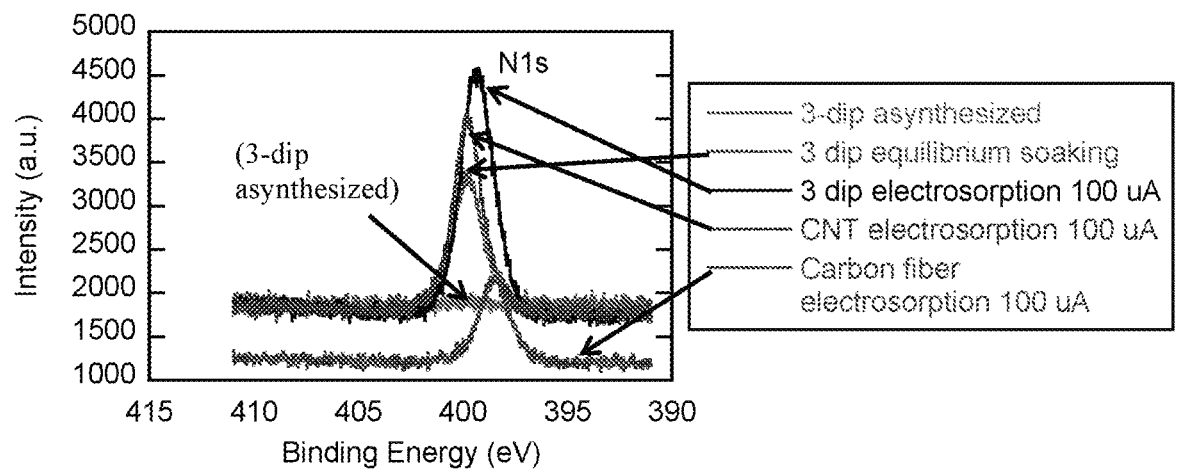
FIG. 9 shows the high-resolution N1s spectra of various electrode substrates before and after adsorption.
Figure 10:
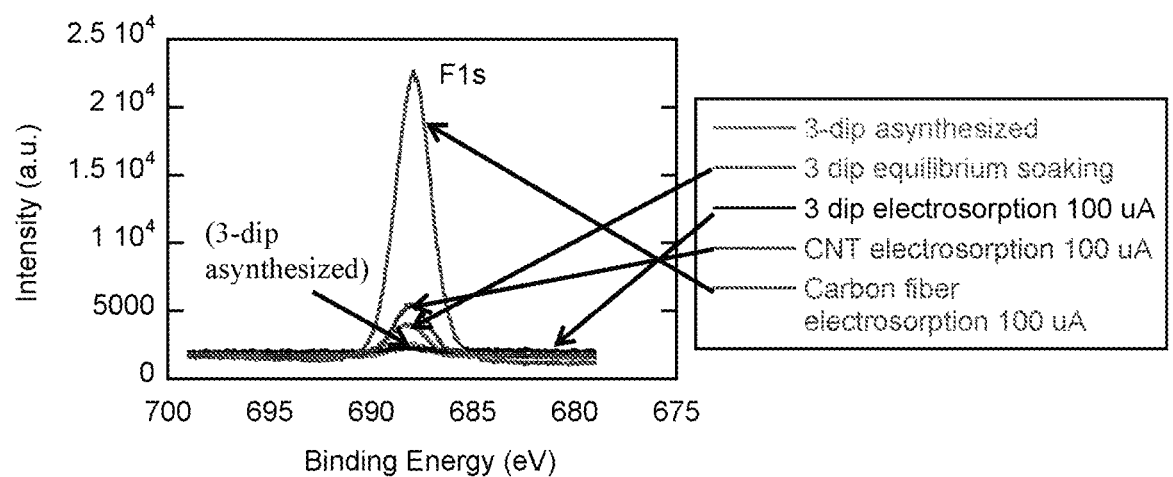
FIG. 10 shows high-resolution F1s spectra of various electrode substrates before and after adsorption. The ratio of N1s integration to F1s integration correlates with the amount of protein adsorbed on the surface.
Figure 11:
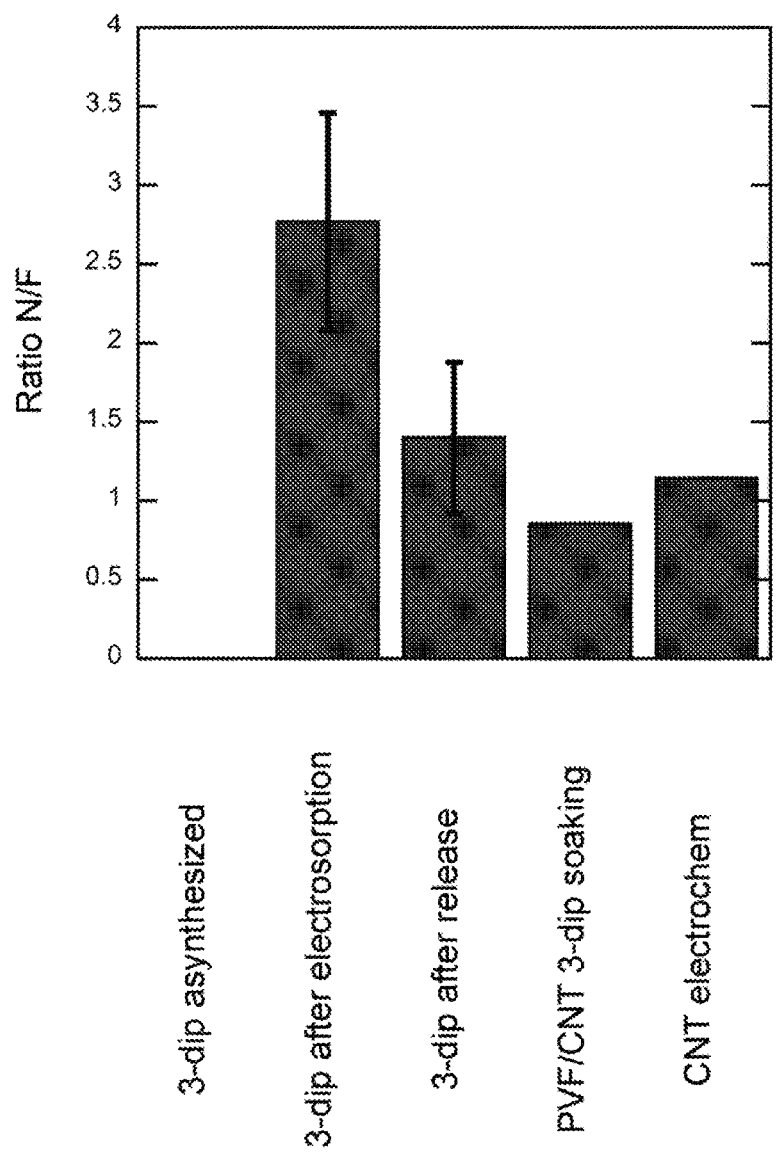
FIG. 11 is a graph showing the XPS ratio of nitrogen to substrate fluorine.

The immobilization efficiency of the protein on the electrodes was investigated by assaying the liquid-phase by BCA as well as the characterizing the surface chemistry by XPS during the adsorption and desorption process (FIG. 5A). During an adsorption-desorption cycle (adsorption at pH=11 and desorption at pH=7 of α-CHY), the degree of "leached" enzyme was estimated. In the first step, the protein is adsorbed from a 1 mg/mL pH=11 solution. Under oxidation, at application of potential at +0.4V, the electrode was transferred to a fresh 50 mM solution at pH=7. Under oxidation, the surface-bound α-CHY was highly stable, with less than 1 µg detectable enzyme present in solution when assayed by BCA, indicating that no protein desorbs by pH effects, and that the ferrocenium-anionic complexes are highly stable. After switching off the potential, at pH=7, ~15 µg desorbs through inherent self-discharged; and upon application of forced 0 or negative potential, all the remaining protein desorbs (FIG. 5B). XPS analysis of the surface of the fibers indicated that most of the protein adsorbed was effectively desorbed (>95%) after electrochemical reduction (FIG. 5C), as reflected by the ratio of the N1s peak to the F1s. The fluorine serves as an internal standard for the hydrophobic Teflon-treated carbon fibers, and when protein is adsorbed, no fluorine can be detected as it is under a layer of adsorbed protein. This stability under oxidation makes the system perfectly suitable for heterogeneous immobilization of enzymes. High-resolution quantification of the integrated F1s and N1s peaks are shown in in FIGS. 9-11.

Enzyme Kinetics.

Figure 6A:
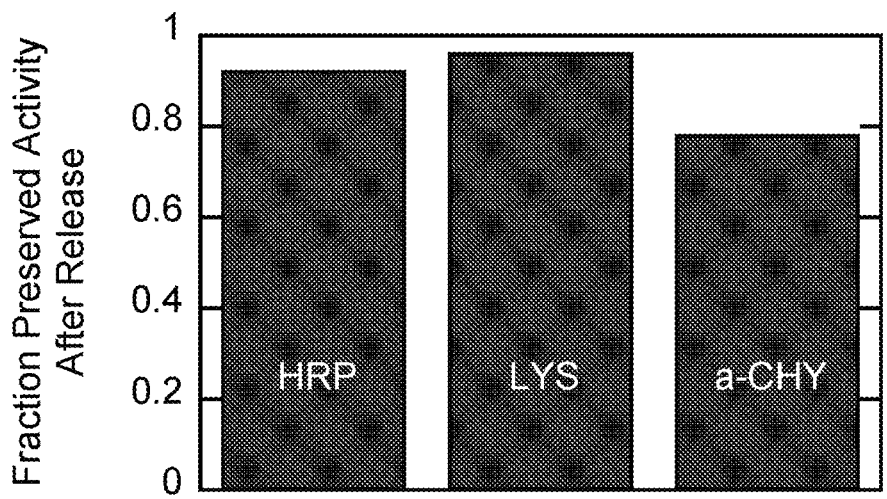
FIG. 6A shows the comparison of enzyme activity in released forms between all three enzymes after once cycle of oxidation and reduction (pH=7 in 50 mM phosphate).
Figure 6B:
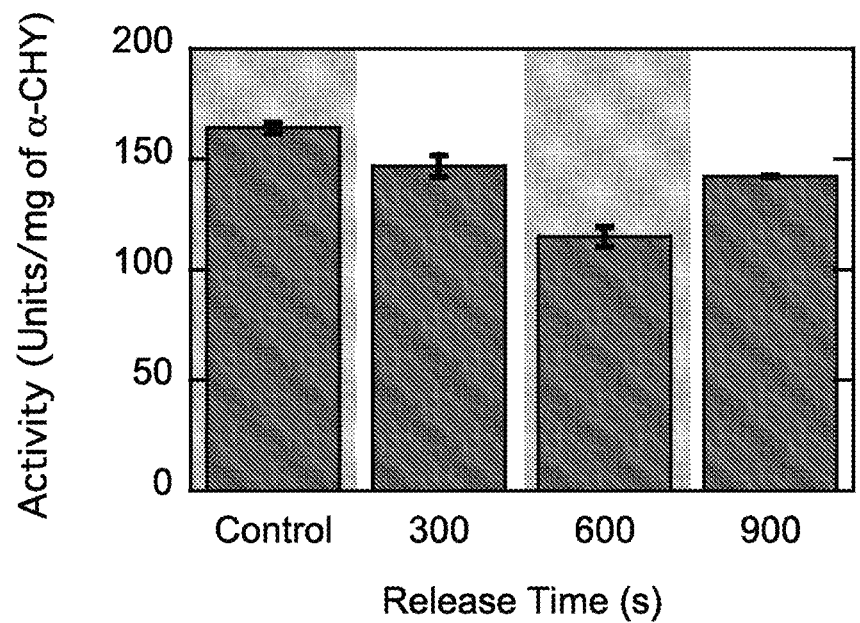
FIG. 6B shows the time dependence of electrochemical treatment on enzyme activity under various oxidation lengths.
Figure 13:
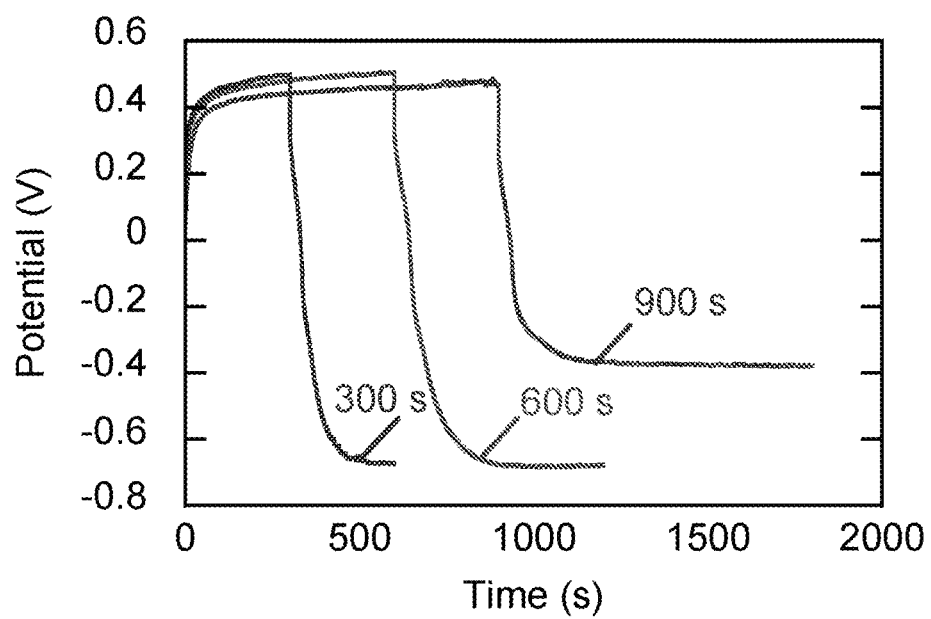
FIG. 13 shows the preservation of α-chymotrypsin enzyme activity at different release conditions for different electrochemical treatment times.

To determine the effect of the electroactive surface on the structure and biological activity of the proteins, enzymatic activity was evaluated for lysozyme, HRP and α-CHY. It is shown that 80-100% of the activity was retained after release (FIG. 6A). The loss in activity was also found not to be dependent on the duration of the oxidation or reduction steps, with α-CHY retaining around 80% activity even after longer intervals of electrochemical treatment (FIG. 6B). The activity was found to be approximately the same under 300, 600 and 900 seconds of oxidation (FIG. 13). However, with higher potentials than the ferrocene oxidation potential under chronoamperometry, the enzyme activity was severely affected (~20-30% at 0.7 V), similar with lower reductions (<−0.5 V). Mechanistically, this biocompatibility can be attributed to the constant potential of the redox process, which prevents higher overpotentials that would otherwise compromise chemical structure and decrease biological activity. The interaction of the proteins with the poly(vinyl) ferrocene stems primarily from the non-covalent or electrostatic/donor-acceptor binding of the exposed protein carboxylate groups with the various oxidized ferrocenium sites on the electrode surface.

Figure 6C:
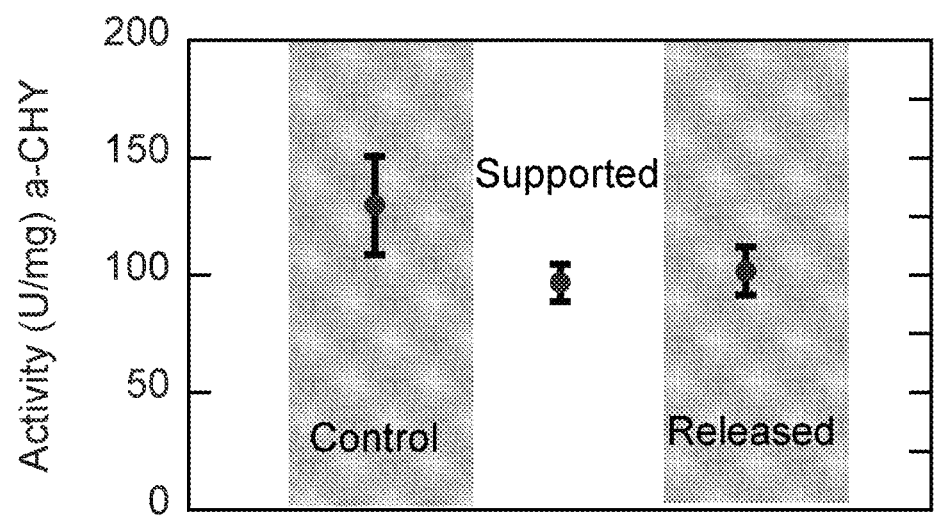
FIG. 6C shows a comparison of α-CHY enzymatic activity when immobilized on PVF/CNT.
Figure 6D:
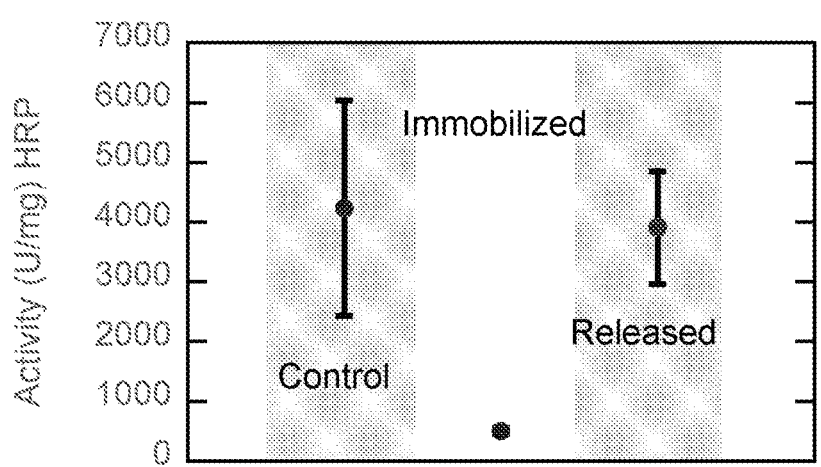
FIG. 6D shows a comparison of enzymatic activity of HRP when supported on PVF/CNT at pH=7, 50 mM phosphate.

Electrostatics is a powerful mechanism for attachment of charged catalysts, as it does not require a direct chemical bond, and thus minimally affects activity while still providing stability against leaching. Stable immobilization is crucial for the design of heterogeneous catalysts as it allows recovery and re-use of the catalytic material. Horseradish peroxidase (HRP) and α-chymotrypsin (α-CHY) were chosen as models for immobilized enzyme catalysis. HRP in particular is a heme-containing enzyme that can catalyze oxidation of a wide variety of organic and inorganic compounds (e.g., as described in Veitch, N. C. Phytochemistry 2004, 65, 249) and has received intense attention in biology and biotechnology, such as the use of HRP C for enantioselective oxidations as an alternative to organometallic catalysts. Similarly, α-CHY is a model hydrolytic enzyme that has been covalently attached or impregnated into porous material. FIG. 6C shows that the activity of α-CHY is retained to a high degree (75%), which compares very favorably with the results for similar covalently bound α-CHY. For example, α-CHY bound covalently to magnetic nanoparticles through amino-functionalization was shown to retain 59% of its activity for hydrolysis, and in polymeric fibers, around 65% of α-CHY was retained. Horse-radish peroxidase (HRP), on the other hand, suffered a significant decrease in activity (with retention of only 12-17% of the native activity) when adsorbed to the electrodes (FIG. 6D), although this value does compare favorably with activity retention with other known methods of immobilization (~1% on poly(2-hydroxyethyl methacrylate, 2.5-12% on multi-walled carbon nanotubes, and 5% in mesoporous silica). This loss of activity of HRP has been attributed to changes in protein conformation upon surface adsorption and porous confinement. However, it could also be due to interference from the electrochemical potential from the redox surface on the active center of the enzyme.

However, upon release, the enzyme preserves its activity. The strength of attachment of the proteins to the electrode, after oxidation in the presence of a 1 mg/mL α-CHY stock solution and surface cleaning, was evaluated by replacing the original solution with fresh, protein-free buffer, and no protein leaching was observed into the new buffer by BCA. In addition, upon removal of the electrode, no further enzyme kinetics was observed in solution. Also, PVF-CNT itself does not catalyze any of the aforementioned tested reactions, in a blank control. Overall, the activity retention of both α-CHY and HRP bound to oxidized PVF/CNT surfaces was found to be comparable to, and often better than, many existent porous confinement materials. A possible mechanism for this stable attachment may be the creation of redox-mediated hydrogen bonds between the pockets of anionic carboxylates in the protein and the ferrocene surface which acts as an anchor. These results show the great potential of these materials as non-destructive, electrochemically-controlled bio-catalyst support, and their effectiveness as non-destructive, electrochemically-reversible adsorbent materials.

Summary

Poly(vinyl)ferrocene-functionalized electrodes showed dramatic increase in affinity with proteins due to specific interactions upon oxidation of the redox-centers. The sorption and release processes were shown to be reversible for bio-macromolecules across a range of pH and ionic strength conditions, selective towards target proteins based on surface affinity with the electrochemically-charged interface, and protein structure and activity were preserved due to the pseudocapacitive nature of the charging process. A constant electrochemical potential was sustained during adsorption and desorption by the redox process of ferrocene, thus preventing any side reactions that would be harmful to the chemical structures of the biomacromolecules and affect activity. Thus, significant enzyme activity was found to be preserved upon immobilization for HRP and α-CHY when compared to existing support methods. In addition, the activity of the immobilized enzyme was found to be fully recovered after desorption. In sum, this Example presents the novel design and utilization of smart redox-materials for tuning surface-biomacromolecule interactions, which can increase efficiency of electrochemically-driven bioseparations, redox-mediated electrochemical release devices, and heterogeneous biocatalysis through specific non-covalent interactions.

Experimental and Computational Methods.

Electrode Preparation:

The method is based on a facile approach for non-covalent functionalization. The electrodes were prepared by cutting 2 cm by 1 cm conductive carbon paper from Electrochem Inc., then soldered with copper tape. Two stocks were prepared: stock A of 80 mg poly(vinyl)ferrocene (PVF) (Polysciences, Inc.) and 40 mg multiwalled CNT in 10 mL anhydrous chloroform, and stock B with 40 mg multiwalled-CNT (MWCNT, Sigma). The two stock solutions were sonicated for 2 hrs in icy water to optimize dispersion level. The PVF/CNT(1:1) ratio was prepared by mixing stocks A and B in a 1:1 ratio: 1 mL of A was mixed with 1 mL of B and sonicated for another 3 hrs in an ice-bath. Once prepared, the electrodes were dip-coated into the solution with the active material—3 s of contact time for each dip, and leaving to dry for 15 s in between at 25° C.

Protein Concentration Measurements:

Proteins were obtained from SIGMA-Aldrich in lyophilized form: bovine serum albumin (BSA), alpha-chymotrypsin (type II, from bovine pancreas), myoglobin (from equine heart), lysozyme (human recombinant) and ribonuclease A. Protein solutions were prepared with phosphate buffer (50 mM, pH 7) by using different concentrations of $NaH_2PO_4^-$ to $Na_2HPO_4$. For some alternative studies, pH=7 TRIS buffer was used with very small aliquots of HCl and NaOH to perform fine control. Sodium carbonate was used for pH=11, and citrate was used to buffer at pH=5. All solutions were prepared in deionized water. For the protein assays, a two-component Pierce bicinchoninic acid assay kit was used (Pierce BCA, Thermo-Scientific) for measurement of total protein concentration at A562 nm. The micro-BCA assay kit was used, with a linear range between 5 μg/mL to 20 μg/mL, with two to threefold dilutions being performed. For selectivity studies, a GE Äkta Prime fast protein liquid chromatography (FPLC) was used with a size exclusion column GE Superdex 75 10/300 GL. The buffer for elution was PBS at a flow-rate of 0.75 mL/min, with 250 μL of sample and a UV-detector at 280 nm.

Protein Reagents and Measurements:

Proteins were obtained from SIGMA-Aldrich in lyophilized form: bovine serum albumin (BSA), alpha-chymotrypsin (type II, from bovine pancreas), myoglobin (from equine heart), lysozyme (human recombinant) and ribonuclease A. Protein solutions were prepared with phosphate buffer (50 mM, pH 7) by using different concentrations of $NaH_2PO_4^-$ to $Na_2HPO_4$. For some alternative studies, pH=7 TRIS buffer was used with very small aliquots of HCl and NaOH to perform fine control. Sodium carbonate was used for pH=11, and citrate was used to buffer at pH=5. All solutions were prepared in deionized water.

For the protein assays, a two-component Pierce bicinchoninic acid assay kit was used (Pierce BCA, Thermo-Scientific) for measurement of total protein concentration at A562 nm. The micro-BCA assay kit was used, with a linear range between 5 g/mL to 20 ug/mL, with two to threefold dilutions being performed.

Materials Characterization:

X-ray Photoelectron Spectrometry (XPS).

The Physical Electronics Versaproble II X-ray Photoelectron spectrometer was used for the analysis of the surface of the electrodes. The analysis was performed at ultra-high vacuum (1e-08 bar) with an argon-gun neutralizer. The survey scans were performed with 10 cycles from 1400 eV to 50 eV at 200 kV with a pass energy of 80 eV and a step size of 0.5 eV. The high resolution scans for were performed with 100 kV, a pass energy of 11 eV, 0.05 eV resolution with 30 cycles for iron and 8 cycles for the remaining elements. The scans were exported using CASA XPS commercial software and peak fitting was performed using XPS Peak Fit free-ware.

Scanning Electron Microscopy (SEM).

The surface morphology of the electrodes were characterized by a FEG-XL-30 field-emission SEM at 20 kV using a beam size of 3 and high vacuum conditions, and a ZEISS Merlin High-Resolution SEM at 5 kV-20 kV.

Electrochemical Separation.

The adsorption tests were performed in 10 mL BASi MCA cells in the three-electrode configuration. A platinum wire was used as the auxiliary electrode, and references electrodes of a platinum wire in $Ag/Ag^+$ were used. 5 mL of 1 mg/mL protein solution were the standard electrosorption conditions. All electrochemical studies were performed on a VersaSTAT 4 potentiostat (Princeton Applied Research) with automatic IR compensation between 50 MΩ and 5Ω. A custom-made, 3-D printed electrochemical cell was also used for low-volume electrosorption and release cells, with the possibility of multi-stack and thus a much higher surface area to volume ratio.

Enzyme Kinetics Assay:

All enzyme kinetics assays were performed with appropriate colorimetric substrates (purchased from SIGMA-Aldrich) which could be assayed at a variety of wavelengths, as describe below. The enzyme activity was obtained by obtaining the highest slope at the wavelength $A_\lambda$ and calculated using the following formula:

$$\text{Activity} = \frac{\frac{dA}{dt}}{\epsilon} \frac{df}{C_E \cdot V}$$

Lysozyme (LYZ):

For the enzyme activity assay, ultrapure water (>18 mΩ water) was used. A 0.01% (w/v) *Micrococcus lysodeikticus* cell suspension was prepared in 66 mM potassium phosphate buffer (pH to 6.2 at 25° C.).

α-Chymotrypsin (α-CHY):

To assay the activity of free alpha-chymotrypsin, a solution containing 100 μL water, 50 μL 500 mM TRIS HCl pH 7.5, 12 μL calcium chloride, and 38 μL 20 mM Suc-AAPF-pNA (in DMSO) was preheated at 37° C. for 1 minute. The reaction was then initiated by adding 100 μL of the enzyme sample to the solution. The enzyme-substrate mixture was incubated at 37° C. and shaken at 1400 rpm; to detect the progress of the reaction, every 60 seconds, 50 μL of the enzyme-substrate mixture was added to 150 μL of 2 M acetic acid stop solution, yielding 5 time-data points. The progress of the reaction at each time-point was then analyzed in duplicates via UV absorbance at 410 nm.

The activity of immobilized alpha-chymotrypsin was similarly detected with minor modifications. First, the volume of Suc-AAPF-pNA solution was increased from 200 μL to 0.9-1 mL. Electrode samples containing absorbed proteins were cut into approximately 3 mg samples (containing approximately 5 μg of protein) and added to the solution to initiate the reaction. The mixture was shaken at approximately 1400 rpm at room temperature. To assess the progress of the reaction, 50 μL samples of the Suc-AAPF-pNA-enzyme mixture were added to 150 μL 2 M acetic acid every 60 seconds, yielding 5 time-data points. The progress of the reaction at each time-point was then analyzed in duplicates via UV absorbance at 410 nm.

Horse-Radish Peroxidase (HRP):

To assay the activity of free HRP enzyme, 750 μL of TMB was preheated at 25° C. for 1 minute. The reaction was then initiated by adding 15 μL of the enzyme sample to TMB solution. The enzyme-TMB mixture was incubated at 25° C. and shaken at 1400 rpm; to detect the progress of the reaction, every 30 seconds, 120 μL of the enzyme-TMB mixture was added to 48 μL of 1 M phosphoric acid stop solution, yielding 5 time-data points. The progress of the reaction at each time-point was then analyzed in duplicates via UV absorbance at 450 nm.

The activity of immobilized HRP enzyme was similarly detected with minor modifications. First, the volume of TMB was increased from 750 μL to 10 mL. Electrode samples containing absorbed proteins were cut into approximately 3 mg samples (containing approximately 5 μg of protein) and added to the TMB to initiate the reaction. The mixture was shaken at approximately 1400 rpm at room temperature. To assess the progress of the reaction, 120 μL samples of the TMB-enzyme mixture were added to 48 μL 1 M phosphoric acid every 15 seconds, yielding 5 time-data points. The progress of the reaction at each time-point was then analyzed in duplicates via UV absorbance at 450 nm.

Immobilized Enzyme Kinetics:

For heterogeneous enzyme activity, the electrode was removed from the protein solution under oxidation and washed with fresh buffer to remove any weakly, non-bound protein. The electrode was then placed into a fresh solution of the substrate, corresponding to the enzyme testing, and the activity of the bound enzyme was estimated by taking 30 s time interval absorbance readings. The activity was normalized to enzyme mass based on the amount of enzyme bound (based on electrosorption tests). No leached enzyme activity was expected as substrate solution had no detectable enzyme by assay, in addition, upon removal of electrode no further product conversion was observed.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, the term "about" generally means within 10% of an indicated value. In some embodiments, the term "about" means within 5% of an indicated value.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of separating a target biomolecule from an aqueous solution comprising:
contacting the aqueous solution with: (i) a first electrode comprising a first substrate and a first redox species immobilized to the first substrate, wherein the first redox species is selective toward a target functional group of the target biomolecule based on a specific chemical interaction between the first redox species and the target functional group, wherein the specific chemical interaction is activated by a Faradaic/redox reaction; and (ii) a second electrode; and
applying an electrical potential across the first electrode and the second electrode such that the first redox species transforms from a first redox state to a second redox state and binds to the target functional group of the target biomolecule present in the aqueous solution, thereby separating the target biomolecule from the aqueous solution.

2. The method of claim 1, wherein the target biomolecule is selected from the group consisting of proteins, nucleic acids, viruses, bacteria, peptides, amino acid fragments, antibodies, enzymes, sugars, fatty acids, lipids, vitamins, co-enzymes, and combinations thereof.

3. The method of claim 1, wherein the first redox species is an organometallic compound or metallocene, an organic species or organic polymer, a crystalline solid, a cyclodextrin-based system, a metal-polypyrridyl system, a metal dicarbamate, a cryptand, a redox-active arene, a dendrimer comprising a redox-active center, or a redox-active organic macrocycle.

4. The method of claim 1, wherein the first redox species is an organometallic compound or metallocene.

5. The method of claim 1, wherein the target functional group comprises a carboxylate moiety, an amino group, a hydrophobic domain, a hydrophilic domain, and/or a specific charge distribution.

6. The method of claim 1, wherein: (i) the aqueous solution has a pH that is above an isoelectric point of the target biomolecule for anion-selective separation; or (ii) the aqueous solution has a pH that is below the isoelectric point of the target biomolecule for cation-selective separation.

7. The method of claim 1, wherein the aqueous solution has an ionic strength of 0 mM to 10 M.

8. The method of claim 1, wherein the target biomolecule is present in the aqueous solution at a concentration of about 50 µg/mL to about 5000 mg/mL.

9. The method of claim 1, wherein: (i) the first electrode is an anodic electrode having an electrical potential of about 0.1 V to about 0.8 V; or (ii) the first electrode is a cathodic electrode having an electrical potential of about 0 V to about −1 V.

10. The method of claim 1, wherein the target biomolecule has a weight average molecular weight of about 10 kDa to about 100 kDa.

11. The method of claim 1, wherein the second electrode comprises a second substrate and a second redox species immobilized to the second substrate.

12. The method of claim 11, wherein the second redox species is selective toward an ionic species present in the aqueous solution such that the second electrode captures the ionic species.

13. The method of claim 12, wherein the ionic species is a cationic species, optionally which is a positively-charged biomolecule selected from the group consisting of proteins, DNA, RNA, viruses, peptides, amino acid fragments, antibodies, enzymes, sugars, fatty acids, lipids, vitamins, co-enzymes, and combinations thereof.

14. The method of claim 13, wherein the cationic species is selected from the group consisting of heavy metals, transition metals, lanthanides, organic cations, metal-organic cations, alkali metal ions, alkaline earth metal ions, and rare earth metal ions.

15. The method of claim 11, wherein the second redox species is chemically different from the first redox species.

16. The method of claim 11, wherein the second redox species is a charged species.

17. The method of claim 11, wherein the second redox species is a molecule comprising an electron-accepting functional moiety.

18. The method of claim 11, wherein the second redox species is a charged species of the first redox species, optionally wherein the first redox species is selected from the group consisting of quinone-containing polymers, cobaltocenium-containing polymers, polypyrrole, cyclodextrin-based systems, metal-polypyridyl systems, metal-dicarbamates, cryptands, dendrimers comprising redox-active centers, and redox-active organic macrocycles.

19. The method of claim 1, wherein the first substrate comprises multiwalled carbon nanotubes and the first redox species comprises poly(vinyl)ferrocene (PVF).

20. The method of claim 12, further comprising reversing the applied electrical potential to release the bound target biomolecule from the first electrode and/or the captured ionic species from the second electrode.

21. The method of claim 20, wherein the release of the bound biomolecule and/or the captured ionic species is performed: (i) at the same pH as the aqueous solution; or (ii) at a different pH from the aqueous solution.

22. The method of claim 1, wherein the aqueous solution further comprises at least one non-target biomolecule.

23. The method of claim 22, wherein the at least one non-target biomolecule does not comprise the same target functional group as the target biomolecule.

24. The method of claim 22, wherein the at least one non-target biomolecule has a molecular weight that is different from that of the target biomolecule.

25. The method of claim 22, wherein the at least one non-target biomolecule has an isoelectric point that is different from that of the target biomolecule.

26. The method of claim 22, wherein the at least one non-target biomolecule has a charge distribution that is different from that of the target biomolecule.

27. The method of claim 22, wherein the at least one non-target biomolecule has a dipole moment that is different from that of the target biomolecule.

28. The method of claim 24, wherein the at least one non-target biomolecule comprises a functional group that is the same as the target functional group of the target biomolecule.

* * * * *